US012390335B2

(12) United States Patent
Ahmadi et al.

(10) Patent No.: US 12,390,335 B2
(45) Date of Patent: Aug. 19, 2025

(54) IMPLANTABLE EXPANDABLE BONE SUPPORT DEVICE

(71) Applicant: AM Solutions Holding B.V., The Hague (NL)

(72) Inventors: Seyed Mohammad Ahmadi, The Hague (NL); Banafsheh Sajadi, The Hague (NL)

(73) Assignee: AM Solutions Holding B.V., The Hague (NL)

( * ) Notice: Subject to any disclaimer, the term of this patent is extended or adjusted under 35 U.S.C. 154(b) by 636 days.

(21) Appl. No.: 17/442,074

(22) PCT Filed: Apr. 10, 2020

(86) PCT No.: PCT/NL2020/050246

§ 371 (c)(1),
(2) Date: Sep. 22, 2021

(87) PCT Pub. No.: WO2020/209722

PCT Pub. Date: Oct. 15, 2020

(65) Prior Publication Data

US 2022/0168113 A1 Jun. 2, 2022

(30) Foreign Application Priority Data

Apr. 11, 2019 (NL) .................................... 2022922

(51) Int. Cl.
*A61F 2/44* (2006.01)
*A61F 2/46* (2006.01)
*A61F 2/30* (2006.01)

(52) U.S. Cl.
CPC .............. *A61F 2/44* (2013.01); *A61F 2/4611* (2013.01); *A61F 2002/30266* (2013.01);
(Continued)

(58) Field of Classification Search
CPC .............................. A61F 2/4455; A61F 2/447
See application file for complete search history.

(56) References Cited

U.S. PATENT DOCUMENTS 6,127,597 A 10/2000 Beyar et al.
8,535,380 B2 9/2013 Greenhalgh et al.
(Continued)

FOREIGN PATENT DOCUMENTS

DE 10 2015 110 202 B3 6/2016
EP 3 092 976 A1 11/2016
(Continued)

OTHER PUBLICATIONS

International Search Report and Written Opinion in International Application No. PCT/NL2020/050246, mailed Sep. 3, 2020.
(Continued)

*Primary Examiner* — Ellen C Hammond

(57) ABSTRACT

An implantable, expandable bone support device for a bone, such as a vertebra. The device has a pre-shaped bulk block for filling up an intra-osseous implant cavity of the bone. The pre-shaped bulk block is movable to project in an expanded state of the device out relative to a non-expanded shape of the device. The block comprises a load supporting surface for supporting a load acting on the bone, and a fixation interface for interfacing with a pre-shaped fixation which when interfacing holds the pre-shaped block in the expanded state of the bone support device in position, against the load, and inhibits the device from collapsing from the expanded state into the non-expanded state. An actuator interface allows engaging with an actuator for actuating the movement of the bulk blocks along the pre-defined path. The device comprises a guide defining the pre-defined path along which the bulk block is movable.

21 Claims, 17 Drawing Sheets

(52) U.S. Cl.
CPC ............... *A61F 2002/30331* (2013.01); *A61F 2002/30556* (2013.01); *A61F 2002/30579* (2013.01); *A61F 2002/3092* (2013.01); *A61F 2002/4495* (2013.01)

(56) References Cited

U.S. PATENT DOCUMENTS

| | | | | |
|---|---|---|---|---|
| 10,238,443 | B2 | 3/2019 | Seifert et al. | |
| 2003/0004575 | A1* | 1/2003 | Erickson | A61F 2/4455 623/17.15 |
| 2005/0278036 | A1 | 12/2005 | Leonard et al. | |
| 2006/0212118 | A1* | 9/2006 | Abernathie | A61F 2/4455 623/17.11 |
| 2007/0173826 | A1 | 7/2007 | Canaveral et al. | |
| 2009/0024217 | A1 | 1/2009 | Levy et al. | |
| 2009/0292361 | A1 | 11/2009 | Lopez | |
| 2010/0292796 | A1 | 11/2010 | Greenhalgh et al. | |
| 2012/0010668 | A1 | 1/2012 | Shimko | |
| 2013/0197647 | A1 | 8/2013 | Wolters et al. | |
| 2014/0236297 | A1 | 8/2014 | Iott et al. | |
| 2014/0277501 | A1* | 9/2014 | Northcutt | A61F 2/447 623/17.16 |
| 2016/0317188 | A1 | 11/2016 | Oglaza et al. | |
| 2017/0354513 | A1 | 12/2017 | Maglaras et al. | |
| 2018/0078384 | A1* | 3/2018 | Suddaby | A61F 2/4611 |
| 2018/0296361 | A1 | 10/2018 | Butler et al. | |
| 2019/0053912 | A1* | 2/2019 | Suddaby | A61F 2/447 |
| 2019/0083275 | A1* | 3/2019 | Bell | A61F 2/4425 |
| 2019/0274838 | A1* | 9/2019 | Manwill | A61F 2/4611 |
| 2020/0093603 | A1* | 3/2020 | Manwill | A61F 2/447 |
| 2022/0142783 | A1 | 5/2022 | Ahmadi | |

FOREIGN PATENT DOCUMENTS

| | | | |
|---|---|---|---|
| EP | 3 463 202 | A1 | 4/2019 |
| JP | 2003-530915 | A | 10/2003 |
| JP | 2004-522469 | A | 7/2004 |
| JP | 2008-520269 | A | 6/2008 |
| JP | 2011-520580 | A | 7/2011 |
| JP | 2012-509157 | A | 4/2012 |
| JP | 2018-526152 | A | 9/2018 |
| WO | WO 01/54598 | A1 | 8/2001 |
| WO | WO 01/78798 | A1 | 10/2001 |
| WO | WO 02/38062 | A2 | 5/2002 |
| WO | WO 2006/051547 | A2 | 5/2006 |
| WO | WO 2009/147527 | A2 | 12/2009 |
| WO | WO 2010/059866 | A1 | 5/2010 |
| WO | WO 2016/112175 | A1 | 7/2016 |
| WO | WO 2017/042366 | A1 | 3/2017 |
| WO | WO 2017/192525 | A1 | 11/2017 |
| WO | WO 2017/201371 | A1 | 11/2017 |
| WO | WO 2018/163056 | A1 | 9/2018 |

OTHER PUBLICATIONS

International Preliminary Report on Patentability in International Application No. PCT/NL2020/050246, mailed Oct. 21, 2021.

Office Action for Canadian Application No. 3,133,433, dated May 30, 2023.

Patrick et al., Robust sacrificial polymer templates for 3D interconnected microvasculature in fiber-reinforced composites. Composites Part A: Applied Science and Manufacturing. Sep. 1, 2017;100:361-70.

Sun et al., Bio-CAD modeling and its applications in computer-aided tissue engineering. Computer-aided design. Sep. 15, 2005;37(11):1097-114.

Wang et al., Interlocking assembled 3D auxetic cellular structures. Materials & Design. Jun. 5, 2016;99:467-76.

* cited by examiner

IMPLANTABLE EXPANDABLE BONE SUPPORT DEVICE

RELATED APPLICATIONS

This Application is a national stage filing under 35 U.S.C. § 371 of International Patent Application Serial No. PCT/NL2020/050246, filed Apr. 10, 2020, which claims priority to Dutch application number 2022922, filed Apr. 11, 2019. The entire contents of these applications are incorporated herein by reference in their entirety.

FIELD OF THE INVENTION

This invention relates to implantable expandable bone support devices for a bone, such as for a vertebra, of a human or non-human mammal. More specific, the invention relates to implantable device such as useable in percutaneous osteoplasty, vertebroplasty and kyphoplasty. The invention further relates to kits of parts, sets of blocks and methods of placing such device.

BACKGROUND OF THE INVENTION

Trauma and other conditions, like osteoporosis, can lead to parts of bone tissue being weakened, and cause fracture or collapse of the bone. To stabilize the bone and transfer mechanical loads, percutaneous osteoplasty, the injection of bone cements, to stabilize and provide support to the bone is known. Various types of bones may need such stabilization and support.

For example, vertebral body compression fractures frequently result in severe and disabling back pain. Many patients may experience significant morbidity and decreased quality of life secondary to severe pain, prolonged immobilization, kyphosis, pulmonary deterioration, depression, and loss of independence. The most common cause is believed to be osteoporosis, more than 700,000 osteoporosis-related fractures are diagnosed each year in the United States alone. Other causes include primary and metastatic malignancies, trauma, hemangioma, and osteonecrosis. Since medical therapy, such as exercise, physio-therapy, etc. may not provide sufficient or no results in alleviating the symptoms, surgery may be needed.

Vertebroplasty has become a widely used alternative surgical treatment for symptomatic treatment of such fractures of which the symptoms cannot be treated by medical therapy. Vertebroplasty is a minimally invasive image-guided procedure involving the injection of bone cement into a vertebral body fracture in an effort to reduce pain and improve stability of the fracture. Kyphoplasty is a similar procedure, but utilizes an inflatable balloon in an effort to reduce the fracture and to create a cavity, which theoretically allows a safer injection of cement into the fractured vertebral body.

It is known to use in these procedures a vertebral body stent which is expanded in the cavity to prevent the vertebral body from collapsing until the bone cement has hardened. However, the commonly known stents are expandable mesh-wire tubular structures similar to those used in angioplastic stents, and themselves are not capable of withstanding the compressive load acting on the vertebral column. For stabilization and support of the vertebra, the bone cement is thus required.

International patent application publication number WO2010103344 discloses, as an expandable structure alternative to the stent, an expandable implantable device which may be inserted inside a vertebral body, for maintenance and/or restoration of a cavity therein. During surgery, this implant is positioned in the cavity of the vertebra to be restored, and expanded. The device includes a top plate and a bottom plate which can be moved away from each other to expand the stent, and which provide a supporting surface to bear against the bone. A mechanical resistance prevents the expandable implantable device from contracting once it has been expanded. When the device is expanded, the plates thus bear against the bone and support the adjacent bone tissue against the vertical loads acting on the vertebra. Once the device is appropriately positioned, a filler material, such as a bone cement, is injected into the vertebra cavity to fill this void and surrounding bone structures.

A common disadvantage of the known support implants, and method of placing them, described above is that they require the use of bone cement. The intra-bone distribution of the cement is difficult to control and, post-injection, in the vertebra an extra-corporal body is present of which leakage of material is not controlled, and cannot be excluded. It should be noted that this disadvantage applies to other types of osteoplasty where bone cement is injected, such as of the knee or hip.

SUMMARY OF THE INVENTION

The present invention provides a device, a kit of parts, a set of blocks and a method of placing a device as described in the accompanying claims.

Specific embodiments of the invention are set forth in the dependent claims.

These and other aspects of the invention will be apparent from and elucidated with reference to the embodiments described hereinafter.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

FIGS. 5-8 schematically show a second example of an expandable implantable device, in which FIGS. 5 and 6 are exploded perspective views of the parts thereof, FIG. 7A-D illustrated the states of expansion of the expandable implantable device, and FIG. 8 shows a side view of a shielded bulk block.

FIG. 10 illustrates a front view of a vertebra with an access and a trocar inserted there through.

FIG. 11 illustrates a side view of a vertebra with a trocar inserted there through.

FIG. 12 illustrates a side view of a vertebra with a pin inserted there through.

FIG. 13 illustrates a side view of a vertebra with an awl inserted there through.

FIG. 14 illustrates a side view of a vertebra with a drill and tube guide inserted there through.

FIG. 15 illustrates a side view of a vertebra with a tube guide inserted there through.

FIG. 17 illustrates a side view of a vertebra with a drill inserted there through.

FIG. 19 illustrates a side view of a vertebra with an gauge inserted there through.

FIG. 21 illustrates a side view of a vertebra with an implanted device and holder inserted there through.

DETAILED DESCRIPTION OF THE PREFERRED EMBODIMENTS

Details will not be explained in any greater extent than that considered necessary for the understanding and appreciation of the underlying concepts of the present invention and in order not to obfuscate or distract from the teachings of the present invention.

Figure 1:
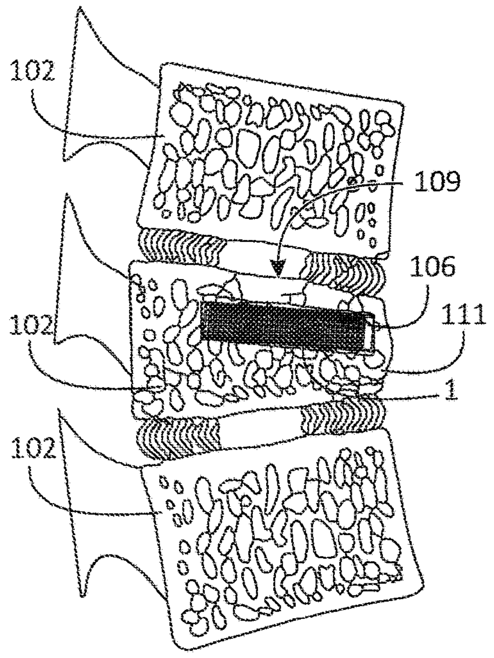
FIGS. 1A-B schematically show a sectional view of a part of the spinal column, in which an example of an expandable implantable device is provided.
Figure 1:
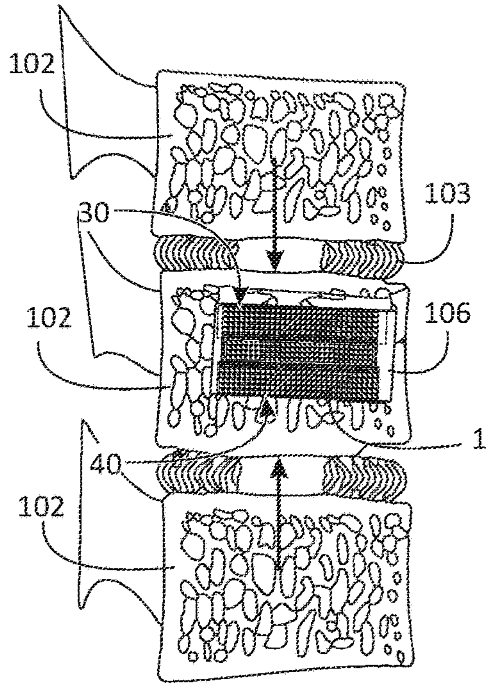
Figure 8:
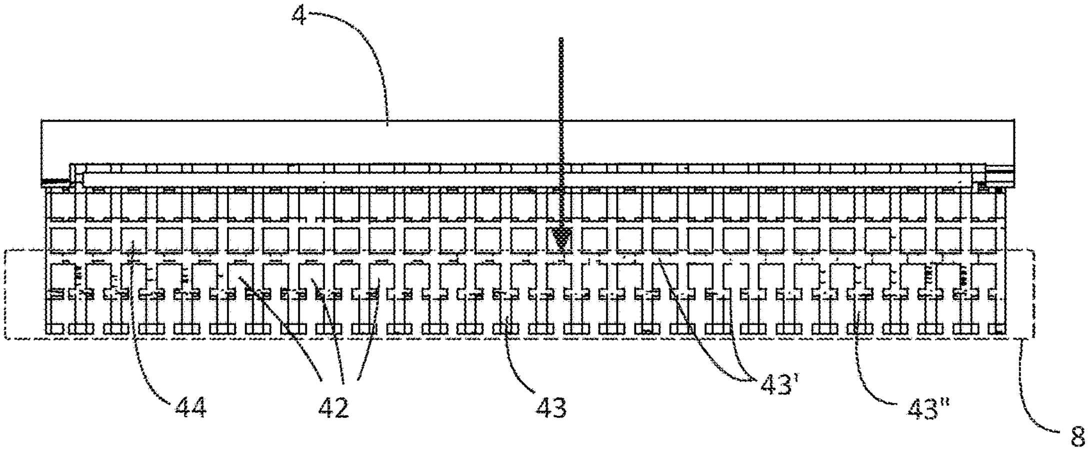

Referring to FIG. 1 the example of an implantable expandable bone support device 1 is implanted in a bone of a mammal, in this example a vertebra 102 of a human. The expandable implantable device 1 can for example be dimensioned for percutaneous placement in the vertebra 102. Typical dimensions of the device 1 (although other sizes being possible as well depending on the cavity in which the device is to be placed) can be a length between 5 mm and 50 mm. For example, the length can be 8 mm or more, such as 15 mm or more. The length can be less than 40 mm, for example less than 30 mm, for instance. A suitable range for the length is a length between 8 and 38 mm. A typical maximum non-expanded diameter can for example be less than 8 mm, such as less than 5 mm, such as 4 mm or less. Preferably, not necessary, that diameter is 1 mm or more, such as 1.5 mm or more. 2.25 mm or more, such as 3 mm or more. A typical maximum expansion of the device is for example between 1.5 and 3 times the non-expanded diameter. Other maximum expansions are likewise possible, and it is currently preferred that the maximum expansion is less than 5 times the non-expanded diameter to ensure a mechanical stable and reliable expansion.

The bone has weakened due to the patient's condition, e.g. osteoporosis or cancer, and has collapsed under the loads that act from the outside on the bone. The load is in this example the compressive load which the spinal column exerts on the vertebral end plates, as indicated with the vertical arrows in FIG. 1 B. Alternatively, the bone could be fractured by an external cause, e.g. by trauma. The device may be used to e.g. treating the weakened bone to restore the bone tissue, or prevent bone collapse, such as caused by osteoporosis or cancer, or healing bone fracture, such as caused by trauma.

In order to stabilize and support the bone, the device is provided in an intra-osseous cavity 106 within the vertebra 102, at the area of the weakened bone. The cavity 106 is surgically made, through a, relatively small, access passage, of which the diameter corresponds to the diameter of the device 1 in a non-expanded state. The device 1 has been inserted into the prepared intra-osseous cavity 106 through this passage.

FIG. 1 A illustrates an implantable device 1 shortly after placement in a vertebra 102. In this example, the passage is a narrow diameter passage which has been created percutaneously, and via the passage the intra-osseous cavity 106 has been created.

In this example, the intra-osseous cavity 106 has been pre-prepared to be located close to the surface of the bone on which the external load acts, in this example the vertebral endplate 109. For example 5 mm or less, such as 4 mm or less, such as 3 mm or less of bone tissue may be present between the top or load bearing surface 30 of the device and the endplate 109. This allows an elastic or plastic deformation of this tissue by the load bearing surface of the device 1 pushing against the vertebral endplate 109 upon expansion and accordingly allows to reduce the risk of bone fracture or collapse when expanding the device 1 (e.g. to partially or completely restore the vertebral height). For instance, 1 mm or more, such as 2 mm or more, for example 3 mm of tissue may be present between the top surface 30 and the vertebral endplate. This reduces the risk that the device 1 pierces through the tissue and becomes exposed during expansion or post-surgery.

Additionally, as illustrated, the device 1 can be positioned close to the anterior wall 111 of the vertebra 102. For instance, the device 1 may be positioned such that there is 1 mm or more, such as 2 mm or more, such as 3 mm or more of space, e.g. with spongy bone material, left between the device 1 and the anterior wall 111. Preferably, this space is 8 mm or less, such as 6 mm or less, for example 5 mm or less. This allows to avoid piercing of the anterior wall 111 by the device 1. The position of the device 1 may be determined prior to expansion, for instance, via imaging techniques well known in the art, so as to ensure the device is fully inside the vertebral body, and e.g. is not in the pedicle.

In FIG. 1 A, the device 1 is still shown in a non-expanded state and is positioned close to the upper vertebral endplate 109. In FIG. 1 B the device 1 is in an expanded state. As shown, in the expanded state the diameter of the device 1 is noticeably larger than in the non-expanded state, and accordingly the device 1 can be brought into the bone with a relatively low invasive surgery, e.g. percutaneously as is explained below in more detail with reference to FIGS. 10-23.

In this application of the device, by expanding the device 1, as can be seen in FIG. 1 B, not only is the bone stabilized against collapse and supported by the device 1, but in addition the vertebra 102 lifted to restore its height, at least to a certain extent but preferably completely.

The device 1 is brought from the non-expanded state into the expanded state by a, not-shown, actuator device which engages with an actuator interface 10 of the device. In this respect, the actuator can be any type of actuator that when engaged at the interface 10 moves one or more of the bulk blocks 3, 4, and various actuators are known in the art. The actuator can for example be a manually, hydraulically, pneumatically, electrically magnetically or mechanically driven actuator and e.g. use a suitable type of mechanical transducer to drive the movement. Generally speaking, the actuator can be a medically acceptable, i.e. sterile and biocompatible, actuator. The actuator can for example be a linear spreader or a scissor jack or other a linear actuator which can drive the movement of the bulk blocks away from, and optionally back towards, each other, such as a rotary-to-linear actuator or hydraulic or pneumatic actuator. For example, the device can use a classic wedge actuator, a parallel bar and linkage actuator, a screw jack, a cam system, a balloon and bellows system, a longitudinal deformation/crush system (in which longitudinal contraction creates vertical expansion), or a stacking system, to name a few.

The expanded state is the final state in which the device 1 will normally remain post-surgery, that is absent failure of the device, and in which the device 1 stabilizes and supports the bone. In the transition between the non-expanded state and the expanded state, the device will pass through intermediate states, in which the device 1 is partially expanded but not to the extent required to provide the stabilization and support considered necessary by the operating surgeon. In this respect, in the expanded state the device 1 does not need to be expanded to its maximum expansion and depending on the conditions of the bone, support required and load conditions, a surgeon may elect to expand the device 1 to its maximum or to a lesser extent. Once expanded, the state of the device 1 may be finalized, e.g. by securing the parts of the device 1 moved to expand the device 1, such as by securing the position of the position of the bulk blocks 3, 4 in the examples.

Figure 2:
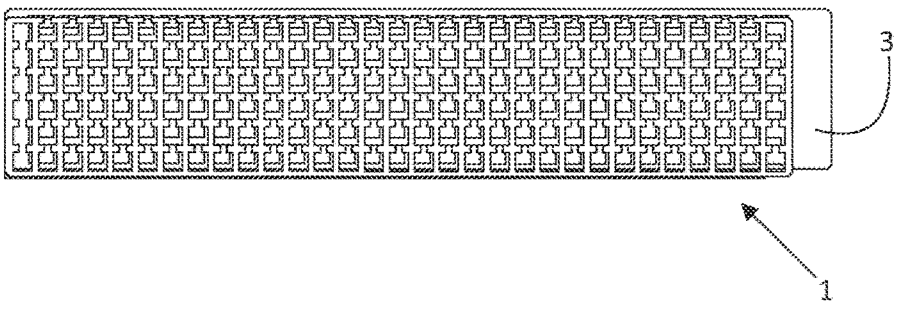
FIGS. 2-4 schematically show side views of a first example of an expandable implantable device.
Figure 3:
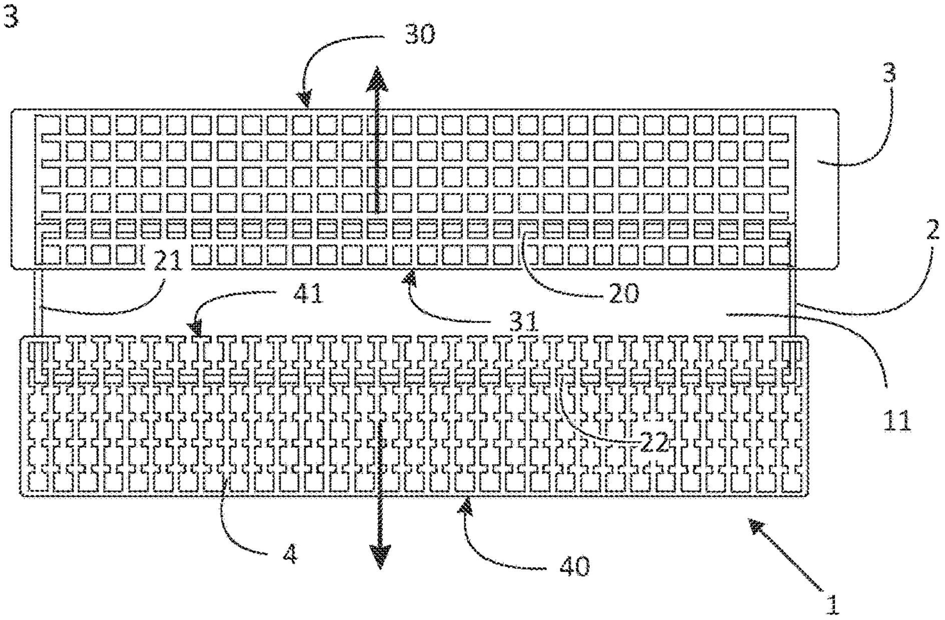
Figure 4:
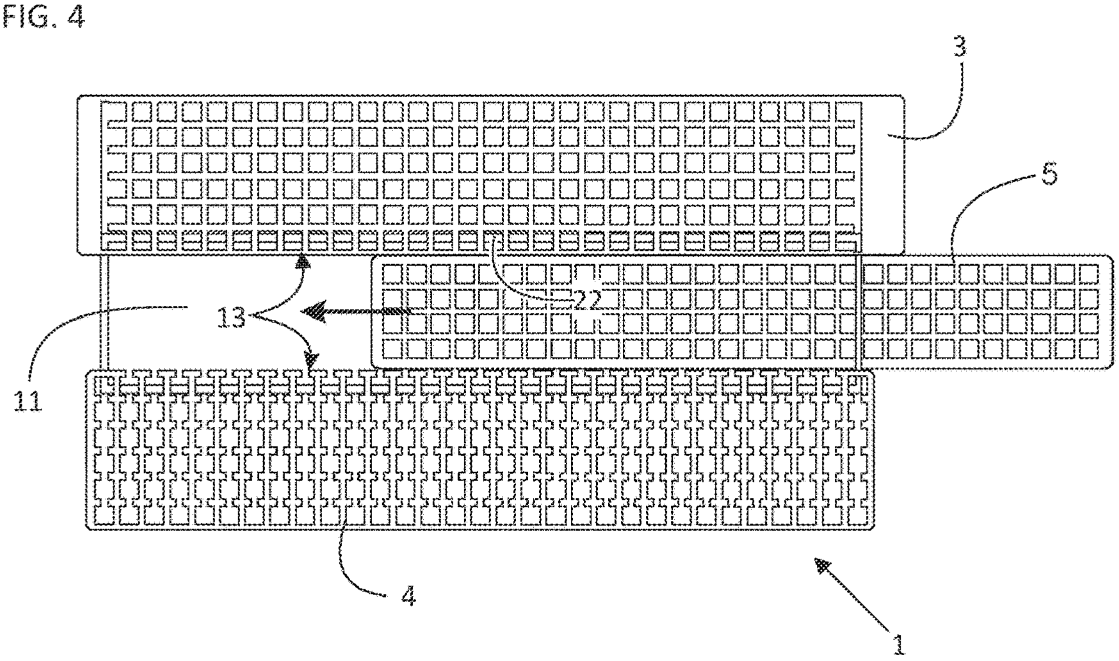
Figure 5:
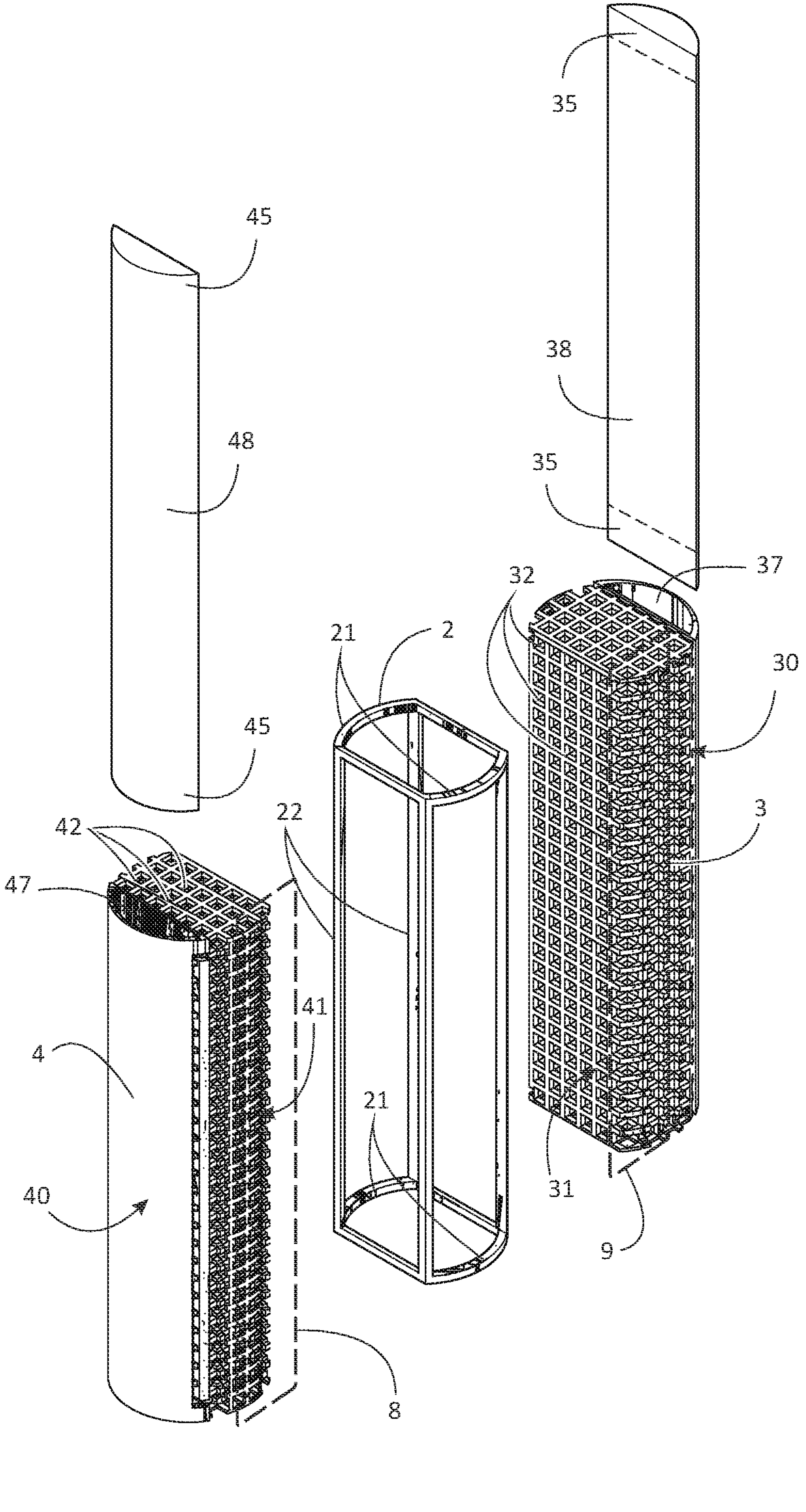

As can be seen more clearly in FIGS. 2-4, the shown device 1 comprises one, or more than one, pre-shaped bulk blocks 3, 4 which fill-up, in the expanded state of the device, the intra-osseous implant cavity 106. Since the cavity 106 is filled up with the pre-shaped bulk blocks 3, 4 the need to e.g. inject bone cement is obviated. However, it will be apparent that some bone cement may be applied for other purposes than filling the cavity and repairing fractures, e.g. bone cement may be provided at the contact interface between the device 1 and the wall, to stabilize and fixate the device 1 to the wall of the cavity 106.

In this respect, depending on the specific implementation, the pre-shaped blocks 3, 4 and if present 5, can fill the overall volume of the implantable expandable bone support device in the expanded state to a percentage selected from the group consisting of: at least 30%, at least 50%, at least 70%, at least 80%, at least 90%, at least 95%, at least 98%. In this respect the overall volume is the volume defined by the outer contours of the device 1 in the expanded state. As shown, in these examples, the pre-shaped bulk blocks 3, 4 completely fill the volume added to the overall volume by the expanding movement of the bulk blocks 3, 4, i.e. the difference in volume between the non-expanded state and the expanded state is filled with the bulk blocks. In the example of FIGS. 5-8 for example, the overall volume is increased about 3× by the movement of the blocks, and as can be seen most clearly in FIG. 7B, about ⅔ of the overall volume is filled with the bulk blocks 3, 4. The bulk blocks completely fill the added volume in this example, but other shapes may be used that could lead to a lower filling grade.

Preferably, the block(s) fill(s) the overall volume completely but optionally less than 100% of the volume may be filled with the blocks. For instance, less than 80%, such as less than 70%, for instance ⅔ of the overall volume may be filled by the bulk blocks in when the device 1 is expanded to the maximum. For example, e.g. in case of a different type of fixation than the fixating block 5 explained below with reference to FIGS. 2-4, the inter-block space 11, which is part of this volume, may be left unfilled or the blocks 3, 4 may have a shape which leaves some parts of the overall volume unfilled, for example when provided with an axial groove at the bone side surface 30, 40. In the example of FIGS. 25-30, for instance, the inter-block space 11 created by the expansion is left unfilled, except for the two fixating blocks 5 that maintain the bulk blocks 3, 4 separated. The overall volume is thus filled in the expanded state to less than 100%, and when maximally expanded, about ⅔ of the overall volume is filled by the bulk blocks in the example of FIGS. 25-30.

The bulk blocks 3, 4 comprise a load bearing surface 30, 40 which as shown with the arrows in FIG. 1 B bears in the expanded state a load exerted by the bone, caused by an external load acting on the bone. The bulk blocks 30, 40 are movable relative to each other in a direction non-parallel to the load-supporting surface, in this example perpendicular thereto as is indicated in FIG. 3 with the arrows.

More specifically, when the device 1 is positioned in the cavity 106 with the surfaces 30, 40 facing the bone, the load bearing surfaces 30, 40 come to contact, and in this example push against, opposite walls of the cavity 106 upon moving the blocks 3, 4. They are inhibited from moving towards each other under the load pressure (when fixated by the pre-shaped fixation). Thus, the device 1 provides support to the bone material present between the load bearing surface 30, 40 and the outside of the bone on which the external load acts. Accordingly, collapse of the bone can be prevented. In this example the outside of the bone is the vertebral end plate 109 which interfaces with the inter-vertebral disc 103, and on which the spinal load acts. The device 1 thus supports the vertebra to resist the spinal load and prevent collapse of the vertebra.

In addition, the bulk blocks 3, 4 reduce the load pressure on the material in the cavity and accordingly shield the cavity, thus allowing bone healing. More specific, by this shielding bone regrowth in the cavity is improved. In addition, the expansion of the device 1 can push this bone material away from the cavity, and thus when appropriately positioned can lift, also referred to as jacking-up, the vertebra to restore its height (or restore the outside shape of another bone).

As can be seen in FIGS. 1 A and 1 B, after implanting the non-expanded device 1, the bulk blocks 3, 4 are moved away from each other, such that the blocks bear against the top and bottom of the intra-osseous cavity. For example, a suitable actuator, such as a screw driven jack or spreader, may engage with an actuator interface 10 of the device 1 to expand the device. The actuator may be removed from the actuator interface when the position of the blocks 3, 4 is secured by a suitable fixation and be taken out of the intra-osseous cavity, through the access and out of the body of the patient, e.g. as in the second example of FIGS. 5-8. Alternatively, the actuator may be left in the intra-osseous cavity, such as in the example of FIGS. 25-30, where the threaded rod 18 remains to retain the fixation blocks 5 in position relative to each other, and to ensure the form closed connection of the bulk blocks 3, 4.

Once secured, the device 1 may osseo-integrate into the surrounding bone tissue, and bone tissue may regrow into the cavity 106. To that end, for example, the internal and/or external surfaces of one, or more than one of the blocks 3-5 can be provided with a growth enhancing coating or may have been sandblasted to enhance the roughness thereof. Furthermore, bone graft material may be provided inside one, or more than one the bulk blocks 3, 4, or other parts of the device 1 in fluid communication with the cavity, in which the bulk blocks 3, 4 are inhibited from moving back to their initial position of the non-expanded state of the device 1.

Referring to FIGS. 2-4, these show the expandable implantable device 1 used in FIGS. 1 A and 1 B in different states in more detail. FIG. 2 shows the expandable implantable device 1 in a non-expanded state, FIG. 3 shows the expandable implantable device in an expanded state. FIG. 4 shows the expandable implantable device in an expanded, and secured, state.

As shown in FIGS. 2-4, the device 1 further comprises a guide which defines the pre-defined path along which the bulk block is movable. In this example the guide is formed by at least one, in the example four, rods 21. The rods 21 extend in the direction of movement of the bulk blocks 3, 4, as indicated in FIG. 3 with the vertical arrows. Each rod 21 has a first rod end and a second rod end, and the range of motion of the bulk block is defined by the distance between those ends. Although other guides are possible as well, the rods in this example, are part of a frame 2 to which the bulk blocks 3, 4 are both movably attached. In this example, the bulk blocks are both movably attached to the frame 2 by a form-closed connection, and can slide along the rods, but are inhibited from moving further by transverse rods 22 of the frame. The transverse rods 22 are, for the respective bulk block, located at the bone side of the frame, i.e. the same side of the frame 2 as the bulk block in question. Each transverse rod 22 connects corresponding ends of multiple spaced apart rods 21. As shown, and can be more clearly seen in FIGS. 5 and 6 with respect to the second example, the frame 2 can have a box-like shape.

Instead of a single frame to which all the bulk blocks 3, 4 are attached, for example multiple frames may be provided or another suitable connection which imposes a maximum distance between the bulk blocks 3, 4 and defines a limited range of motion for the bulk blocks. As illustrated in the example of FIGS. 25-30, for example each bulk block 3, 4 may be movably attached to an intermediate object, in FIGS. 25-30 the rod 18. For example each bulk block 3, 4 may be attached via a form-closed connection, in this example via respective ring-shaped members 62, 63.

In this respect, the term "form-closed" refers to the German term "Formschluss", which is a connection between at least two connected elements formed by the interlocking shapes of the elements and in which the absence of a connecting force does not release the connection. In other words, in the case of a form-closed connection, the shapes of the connected elements are in the way of the other, such that the connection cannot be released without deforming the shapes.

Each of the bulk blocks 3, 4 comprises a fixation interface 13. The fixation interface 13 can interface with a pre-shaped fixation which, when interfacing holds the pre-shaped bulk blocks in the expanded state of the bone support device in position, against the load, and inhibits the device 1 from collapsing from the expanded state back into the non-expanded state. In this example, the interface 13 is formed by inter-block space side surfaces 31, 41 of the blocks 3, 4. As illustrated, an inter-block space 11 is formed by the movement of the bulk blocks 3, 4 away from each other. The inter-block space 11 is in the direction of movement defined by the inter-block space side surfaces 31, 41. Although alternatively, for example, a scissor jack may be provided between the inter-block space side surfaces 31, 41, in this example and as is illustrated in FIGS. 3 and 4, the fixation is implemented as a, suitably shaped and sized, pre-shaped fixation block 5, while in the example of FIGS. 25-30, the fixation is implemented as multiple fixation blocks 5. Referring to the example of FIGS. 3 and 4, the fixation block 5 can be slid into the inter-block space 11, after the device has been deployed in the cavity 106, to inhibit the pre-shaped blocks from moving towards each other. As is apparent from FIG. 4, this inter-block space 11 is thus filled with the fixation block 5. The fixation block 5 may for example be selected from a set (such as of FIG. 24) of fixation blocks of different sizes depending on the size of the intra-osseous cavity 106 created or the observed dimensions of the inter-block space 11 during surgery. It will be apparent though, that in the expanded state the inter-block space 11 can be left empty and not be filled, e.g. in case the bulk blocks 3, 4 are fixated with a scissor-jack placed in the inter-block space 11 which retains the bulk blocks 3, 4 in position.

Once the fixation block 5 has been brought into position, the bulk blocks 3, 4 are inhibited from moving, under the loads acting on the vertebra, back to their initial position. In this example, the bulk blocks 3, 4 are in the other direction, towards the bone, inhibited from moving by the form-closed connection with the frame 2. In the shown example, the fixation block 5 has a substantially cuboid shape but it will be apparent that e.g. a wedge-shaped fixation block (as in the example of FIGS. 25-30) may also be used, in which case the surfaces 31, 41 may e.g. be inclined to define an inter-block space 11 which is tapered towards the front end of the device, seen in the longitudinal or axial direction along which the device 1 is to be implanted. More generically, in case of a wedge-shaped fixation block, or blocks, 5, the surface 31, 41 may be inclined, so that the inter-block space 11 is tapered in the same direction in which the wedge is tapered, at least over the length where the wedge is moved into the inter-block space 11. For instance, as in the example of FIGS. 25-30, where the wedge shaped fixation block 5 is movable from the axial end to a certain depth into the interstitial space 11, the surfaces 31, 41 are at the ends inclined to have a similarly tapered interstitial space over that depth. Said differently in that example at the axial ends the interstitial space is shaped as a wedge-shaped notch between the projecting ends 35, 45 of the bulk blocks. In such a case, for example, the wedge may also serve as actuator and by inserting in the inter-block space 11 widen the inter-block space 11 and move the blocks 3, 4 towards the bone tissue defining the cavity 106.

As illustrated in FIGS. 2-4, the pre-shaped bulk blocks 3, 4 are movable along a pre-defined path to project in an expanded state, shown in FIGS. 3 and 4, out of the device relative to a non-expanded shape of the device, shown in FIG. 2. In the example of FIGS. 2-4 in this respect the device has two bulk blocks, but the device 1 may likewise have only a single or more than two bulk blocks which are movable away from an initial position (and in case of multiple bulk blocks from each other) to expand the device 1.

As is apparent from FIGS. 2-4 and 5-8, one, or more than one, member of the device can have a porous outer surface and/or a porous bulk part. E.g. the pre-shaped bulk blocks 3, 4 and/or the pre-shaped fixation 5, and/or the fixation element 6, and/or the core 7 can have a porous outer surface and/or a porous bulk part. The member can be completely porous or partially porous, and have a homogenous porosity with the same pore size, as in the examples, or have a variable pore size. The pores provide an interface for bone in-growth in the bulk block. This allows an increased integration in the bone because the pores provide an attractive place for bone ingrowth, while the fixating block keeps the bulk block in position against the load acting on the bone. Although other pore sizes may be suitable as well, an average pore size of 0.1 mm or more, such as 0.3 mm or more, and/or for example 1.5 mm or less, such as 0.9 mm or less provides a good osseo-integration. In this respect, the average pore size may be controlled with a precision of 10% or better, for example 1% or better. Obviously, in case of a homogenous porosity all the pores will have the average pore size, but heterogenous porosities are also possible.

Thus, device 1 can osseo-incorporate into the bone, i.e. ingrowth of bone matter inside device 1 can be obtained in addition to bone on-growth on the interfaces between device 1 and the bone, e.g the bone side surfaces 30, 40. Without wishing to be bound to theory, it is currently believed that this can occur because at least some of the outer surfaces and the struts 33, 43 inside the bulk blocks 3, 4 form cell growth substrates. The cell growth substrate can for example proteins, water molecules and/or lipids adsorbed to the surface. Also, the substrate may comprise blood platelets attached to the surface. After formation of the growth substrate, osteoblasts or their progenitors, such as osteochondroprogenitor cells or mesenchymal stem cells, will grow thereon and subsequently form the bone on the surface of the blocks 3, 4, and, if present, of the fixation block 5. In this respect, although FIGS. 2-8 show an enlarged view, it should be borne in mind that in reality the device 1 will be dimensioned to fit into the respective bone and to be provided through a minimal invasive procedure, accordingly the grid or matrixes shown therein have a such as small pitch that they act as pores. This equally applies to the example of FIGS. 25-30, where the open cells 32, 42 will in practice be small enough to operate as pores. Thus, the device 1 operates as a scaffold for the bone tissue. In this respect, the device 1 can be osteoconductive and/or osteoinductive.

As is illustrated in FIGS. 5-8 with the bone side surface 30, 40 of the bulk blocks 4, 5, the member of the device can have a porous bone side surface which has an average pore size which is smaller than the average pore size of porous bulk part. This allows to support the existing bone effectively, while under the surface the device 1 can still osseo-integrate from the other sides of the device 1. In this respect, in particular the load-bearing bone-side surfaces 30, 40 may have a lower porosity and/or pore size to ensure that the pressure at this contact interface does not lead to the existing bone being pressed through the pores. The member can have a porous, inter-block space side, surface 31, 41 which has an average pore size which is the same of larger than the average pore size of the porous bulk of the member. This allows a good inter-pore communication between pores of the different parts, and in particular between the respective member and the inter-block space 11 (or the parts of the device present therein).

For example, the member may have a porosity of at least, or equal to, one of the group consisting of: 70%, 80%, 90% and less than 100%, such as less than one of the group consisting of: 95%, 85%, 75%. The member may have a porosity which (of course) is more than 0%, such as at least 10%, such as at least 20%, such as at least 30%, such as at least 40%, for example at least 50%, such as at least 55%. Currently most preferred is a porosity in the range of 50% to 80%.

The bulk blocks 3, 4 comprise a load facing block 3 with a load facing side on which the load supporting surface 30 is provided. A shielded block 4 is present at another side of the load facing block 3. The shielded block 4 comprising a bone interfacing surface 40 facing away from the load supporting surface 30. The bulk blocks are movable in a direction from the load supporting surface 30 to the bone interfacing surface 40, or vice versa.

In the examples, the combined volume of the bulk blocks in the expanded state is larger than the combined volume in the non-expanded state. Thereby, the dimensions of the passage needed to bring the device into the cavity 106 can remain very small, while the volume filled by the device 1 in the expanded state is relatively large. Accordingly, the surgery required can remain of a low invasive nature. This is in the examples obtained by the top bulk block 3 extending in the non-expanded state through the bottom bulk block, and moving out of the bottom bulk block 4 (and/or vice versa, of course) when the device 1 is expanded. Thus, in the non-expanded state the overall volume is that of the largest one of the blocks whereas the volume of the smaller one of bulk blocks is added to the combined volume in the expanded state. As shown in FIG. 2, in the non-expanded state the blocks 3, 4 almost completely overlap and given that they have roughly the same volume, the combined volume can be doubled and the ratio of the combined volume in the expanded state and the combined volume in the non-expanded state has a maximum of about 2. In addition, since both bulk blocks move, at least partially or completely, out of the volume occupied by tem in the non-expanded state, the overall volume of the device of the device 1 can be multiplied, in this example by a factor of up to about 3.

As illustrated in FIG. 4, in an implanted state the pre-shaped blocks can form a continuous volume with a fixation block 5 provided in the inter-block space 11 between the bulk blocks 3, 4. Thus, the combined volume in the expanded state can be increased beyond the combined volume of the bulk blocks. This allows to further reduce the invasive nature of the surgery. More specific, a device with a large volume in the expanded state can be brought into the bone through a relatively narrow passage.

In the examples of FIGS. 2-8, the blocks 3, 4 are made to movably extend through each other as follows. The shielded block 4 comprises a first matrix 8 of unit cells 42 and the load facing block 3 comprises a second matrix 9 of, open, unit cells 32. The first matrix 8 comprising a first overlapping part which overlaps with at least a second overlapping part of the second matrix through which the first overlapping part extends. The second overlapping part comprises a submatrix in which each cell is formed by open faces of which the edges are defined by an uninterrupted enclosure of struts 33.

In the shown examples, the first overlapping part and the second overlapping part, and more in general the blocks 3-5, comprise a three dimensional arrangement of n by p by q open cells, with n, p and q being positive integers of at least 2. For example, (n and p) or (p and q) or (q and n) or (p, q and n) may have the same value or have a different value. Any of n, p, and q may be any value out of the group consisting of: 2, 3, 4 5, at least 10, at least 20, at least 50, at least 100, such as at least 200, at least 500 or at least 1000, depending on the specific implementation. The three-dimensional arrangement of the first overlapping part extends through the three-dimensional arrangement of the second part.

The first and second matrix 8, 9 are movable relative to each other to change a combined shape of the blocks 3, 4. In the first overlapping part, each cell comprises struts 43 which form the edges of the open faces 44 of the cell. The struts 43 comprise parallel struts 43" extending in the direction of movement which are uninterrupted. However, of the struts 43, the transverse struts 43' extending transversely to a direction of movement of the pre-shaped block are interrupted, to allow passage of the second overlapping part. The gap in the transverse struts 43' is at least as wide as, or wider than, the thickness of the struts 33 of the second overlapping part to allow them passing through. The second overlapping part extends through the interrupted struts 43' of the shielded block in the non-expanded state.

In the example of FIGS. 5-8, the rods of the frame 2 are thicker than the struts of the second overlapping part. The frame 2 extends in the non-expanded position through a submatrix at the edge of the overlapping part, where the gap is as wide as, or wider than, the thickness of the rods, to allow them passing through and hence the block 4 to move relative to the frame 2. In the cells of the first matrix 8 closest to the inter-block space side though, the gap is narrower than the rods but still wider than the thickness of the struts. Accordingly, the frame is form-closed but movably connected to the shielded bulk block 4 while the load bearing bulk block 3 can completely move, along the predefined path defined by the guide rod 21 of the frame 2, out of the block 4.

Figure 6:
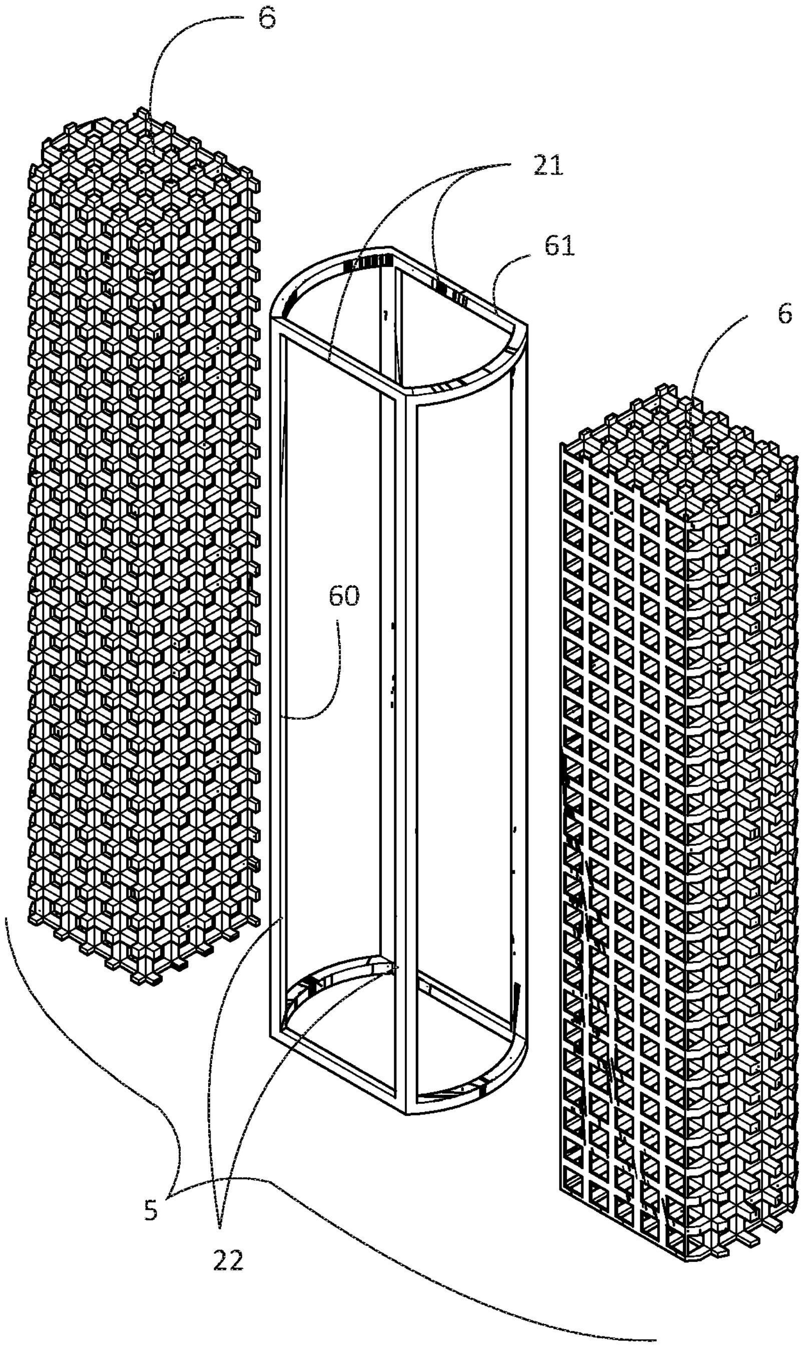
Figure 7:
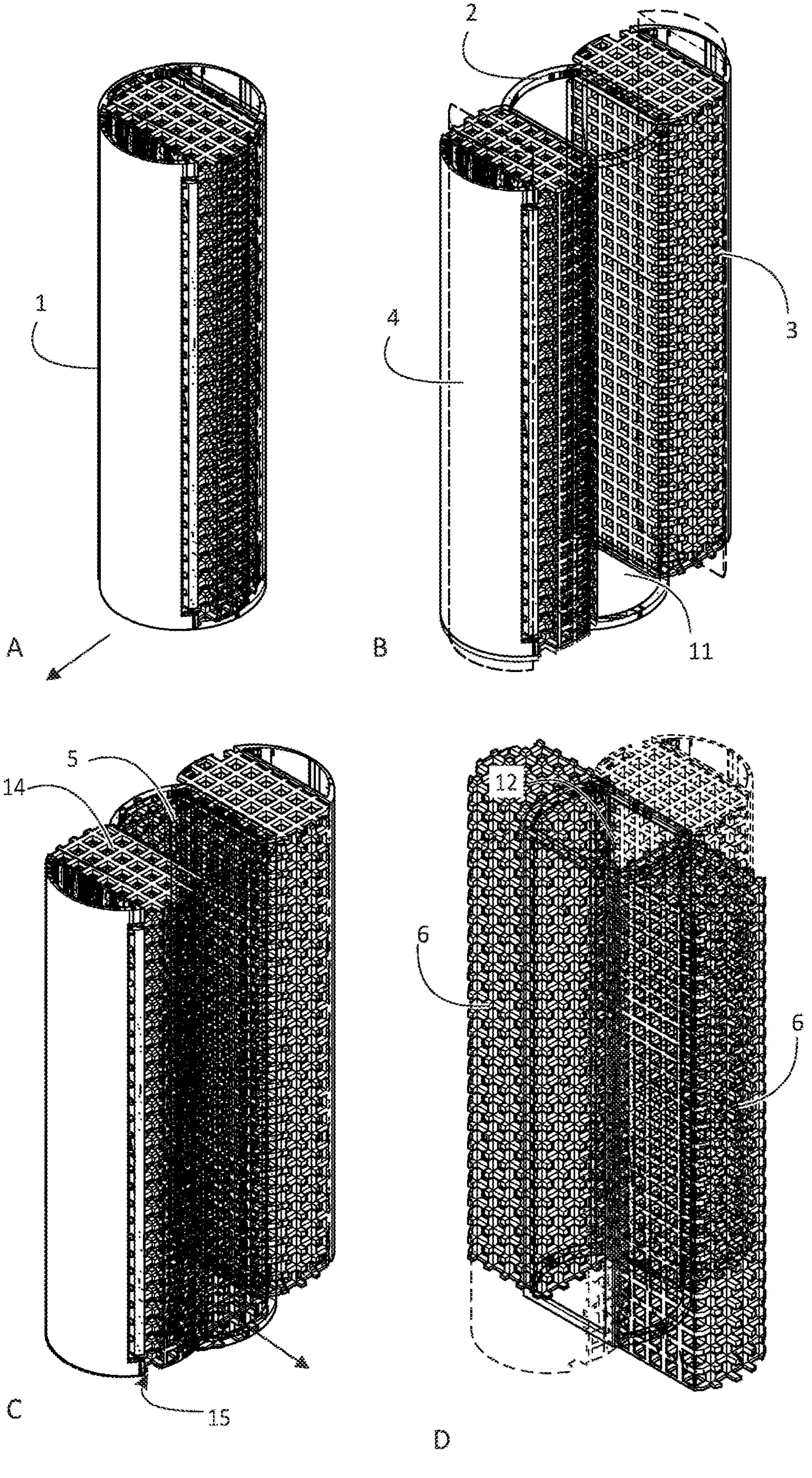

Referring now to the example of FIGS. 5-8, the example shown therein is similar to that of FIGS. 2-4 but differs as described hereinafter. Instead of a monolithic fixating block, the fixating block 5 of this example is expandable and comprises a movable pre-shaped fixation element 6, as illustrated in FIG. 6. A (not shown) pre-shaped element fixation 7 can be inserted in an intra-block space 12 when the element is moved. FIG. 7 A illustrates the non-expanded state, FIG. 7 B illustrates the expansion of the bulk blocks 3, 4. In FIG. 7C, the fixating block is shown slid into the inter-block space 11 in a non-expanded state. As illustrated in FIG. 7, specifically with the arrow in FIG. 7 C, where the fixating block 5 is in position, and with FIG. 7 D where the fixation element is expanded, the fixation element 6 is movable along a predetermined path in a second direction of expansion, e.g. laterally, different from a direction of movement of the pre-shaped blocks 3, 4 to project out of the inter-block space 10.

Subsequently, the movable pre-shaped fixation element 6 may be moved, to project out of the inter-block space 10, thus fixating the device in the second direction, e.g. laterally. In this example, the fixation block 5 has two fixation elements 6 which move in opposite directions, and accordingly the expanded device has a +-shaped cross-section (transverse to the axial direction of the device).

The example of FIGS. 5-8, further comprises a fixation element guide 60 for guiding the movement of the fixation element along the predetermined path. In this example, the guide 60 is formed by a respective ring-shaped member 61 at the axial ends of the fixating block 5, each of which is slideably mounted in the axial ends of both fixation elements 6 with a form-closed connection. The rings thus define the range of motion.

As shown in this example, the fixation elements 6 extent through each other in a manner similar to that of the bulk blocks 3, 4 of the example of FIG. 2-4. Thus, in the expanded state, the combined volume of the fixation element 6 can be increased, and the dimensions of the passage needed to bring the device into the cavity 106 can remain very small, while the volume filled by the device 1 in the expanded state is relatively large. This allows to further ensure or enhance the low invasive nature of the surgery.

Figure 24:
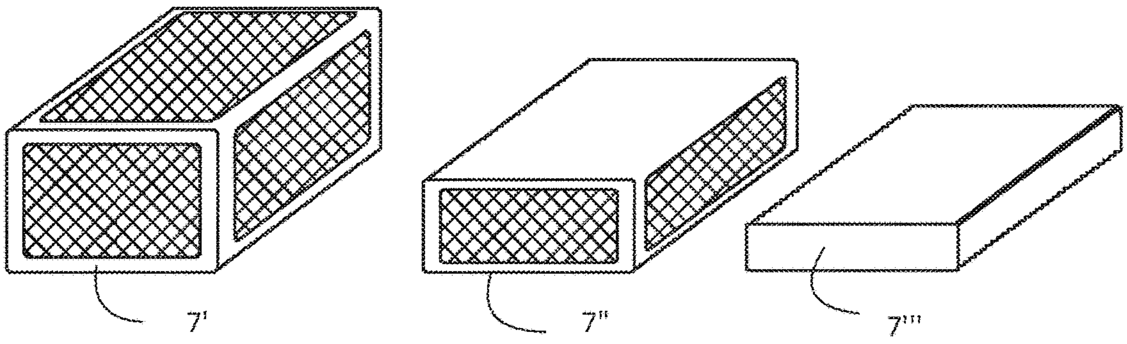
FIG. 24 shows a set of cores which may be used in the examples of an expandable implantable device.

The fixating block further comprises a pre-shaped element fixation for holding the elements in position when the composed shape is expanded, in this example in the form of, not shown in FIG. 7, a pre-shaped, block-like core 7. FIG. 24 illustrates examples of suitable cores 7', 7", 7"". When moving the fixation element 6 to project out of the inter-block space 10, an intra-block space 11 is formed, which is subsequently filled with the fixation core which fits into the intra-block space, thus inhibiting the movement of the fixation element towards the centre of the device and therefore securing the position of the device. Since the rings-shaped members 61 retrain the elements 6 in position in the opposite direction, away from the centre, the position of the elements 6 is thus secured.

In the example of FIGS. 5-8, the bulk blocks 3, 4 further comprise an actuator interface 10 for engaging with a, not shown, actuator for actuating the movement of the bulk blocks 3, 4 along the pre-defined path. In this example, the device 1 has opposite axial ends 14, 15 and the actuator interface 13 comprises a projecting part 35, 45 of the respective bulk block 3, 4, which projects with a respective projecting part 35, 45 beyond an axial end 14, 15, for engaging with the actuator.

The bulk blocks 3, 4 further comprise a passage 37, 47 extending from the first axial end 14 to the second axial end 15, and which is open at both ends. The projecting part forming the actuator interface is here formed by a bar 38, 48 which is inserted in the passage to project with a respective projecting part 35, 45 at one, or more than one axial ends. After actuating the movement of the bulk blocks 3, 4 and securing their position, e.g. by inserting the fixating block 5, these bars 38, 48 can be removed. This allows to avoid unnecessary protrusions with could generate post-surgical complications. The open passage 37, 47 can then be left during recovery fill with regenerated bone tissue.

The porous parts of the constructive elements 3, 4, and generally the constructive elements 3, 4, can be of any suitable type and the first matrix 8 and the second matrix 9 can for example comprise or consist of open cell solid foams. The foam can for example be made of a, biocompatible, metal and be an open cell metal foam. Such a foam can for example be a self-forming structure and form a three dimensional network of cells. The open cell metal foam may for example be reticulate solid foam, as shown in the examples for instance. Also, the foam can be a regular foam or a stochastic foam. In the examples of FIGS. 2-9 for instance, the foam is regular, reticulate foam formed by a matrix of cubic unit cells. A matrix may comprise or consist of a single type of metal foam, but may likewise comprise or consist of a mixture of foams (e.g. of different types of unit cells, such as different geometrical shapes) such as a mixture of reticulated foam with different pore sizes As shown, in these examples, the matrices 8, 9 have a porous inside and at least a part of their surface is open or have outer pores as well. In the example, the outer pores are provided over the complete surface and the matrices are open at all sides. The porous inside is in fluid communication with the outer pores, which allows bone ingrowth into the porous inside. For instance, the inner and outer pores may form an integral network of porous cells. The porous outer surface of the matrices may for example have an openness of at least 5%, for example at least 10%, and preferably at least 50%, such as at least 80%. The openness will of course be less than 100%, and may e.g. be 90% or less, for example less than 70%. The openness is defined as the ratio of the aggregate non-closed areas of the outer pores occupied at the outer surface and the total area of the outer surface.

Figure 9A:
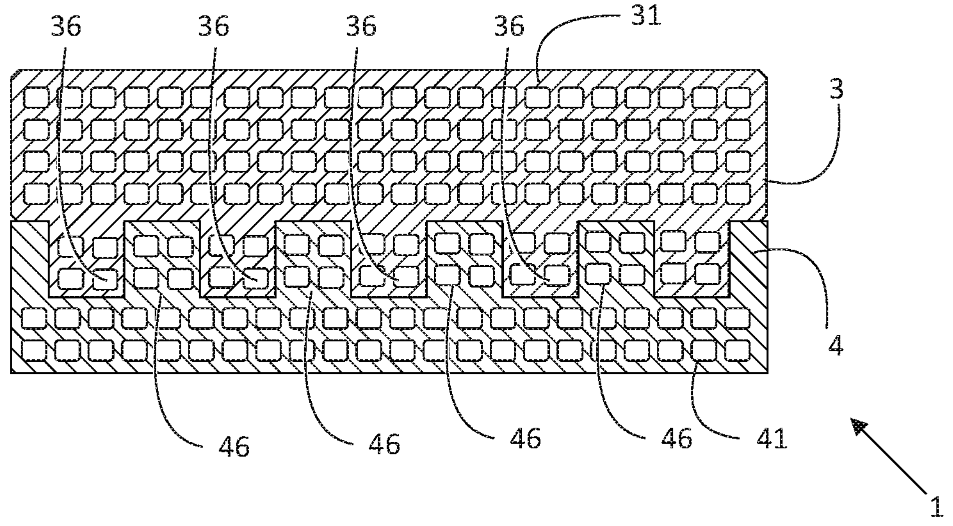
FIG. 9 A and B show side views of a third example of an expandable implantable device in a non-expanded and an expanded state.
Figure 9B:
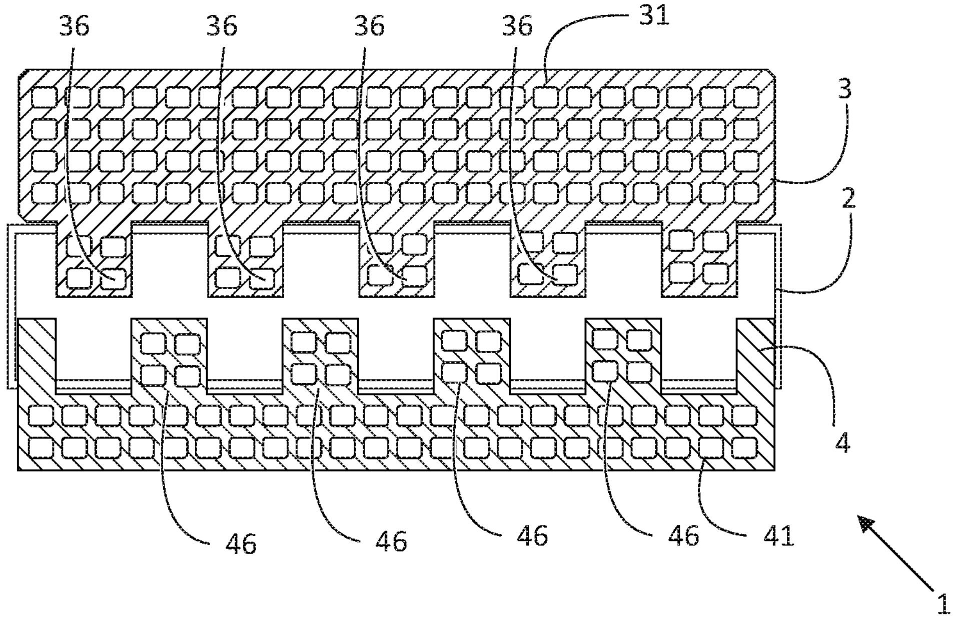

FIG. 9 shows another example, in which like the examples of FIGS. 2-4 and 5-8, the pre-shaped blocks 3, 4 contact each other in a non-expanded state of the device 1, over a respective contact surface, in the examples the inter-block space side surfaces 31, 41. In the expanded state, the contact surface defines a respective side of the inter-block space 11. However, each of the bulk blocks has a comb-shaped inter-block space side with a plurality of fingers 36, 46 which are interdigitated in the non-expanded state. Thus, the diameter of the device can be relatively small in the non-expanded state, whereas in the expanded state the diameter can be increased relative to the non-expanded state.

Figure 10:
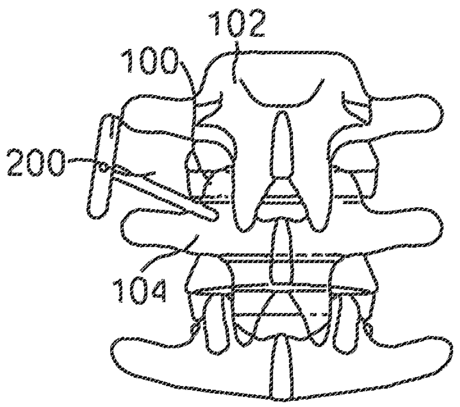

An example of the use of the implantation of a device will now be described with reference to FIGS. 10 to 21. In this example, the device is implanted in a vertebra to stabilize and support the vertebra, e.g. in case of a fracture or a local deterioration of the strength of the bone, e.g. caused by osteoporosis or other conditions. At the beginning, the dimensions of the delivery site are determined, an access angle and path are selected. Subsequently, an access is created and at the delivery site an intra-osseos cavity is created. Referring to FIG. 10, for example a trocar 200 can be positioned, e.g., under fluoroscopic imaging, so as to enter the pedicle 100 between vertebrae 102 and 104 along a frontal plane.

Figure 11:
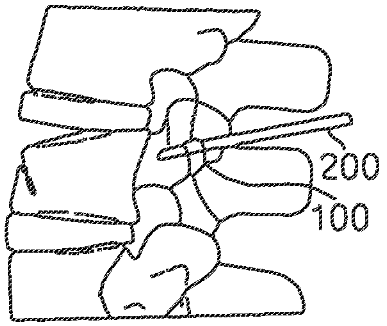

In an alternative, as illustrated in FIG. 11, the trocar 200 may be positioned relative to the pedicle 100 along a sagital plane. The trocar 200 may be driven into the tissue and/or bone so as to achieve an appropriate position, such as, for example, approximately within the first third of the vertebral body 101, so as to fix the axis for the remaining steps of the procedure. The use of an imaging device, such as X-ray imaging, may be used so as to ensure appropriate positioning of the trocar, e.g., along the frontal or sagital plane.

Figure 12:
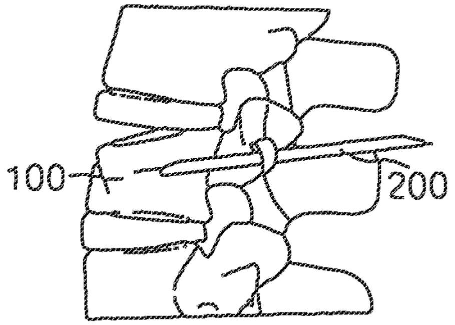
Figure 13:
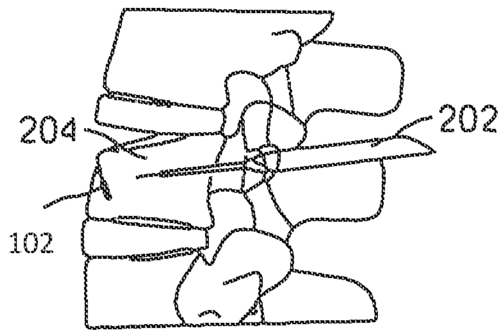

As can be seen with respect to FIG. 12, the stylus of the trocar 200 may be replaced by a pin 202, which pin 202 may be fixed to the medium of the vertebra body 101 and the trocar may then be removed. The use of an imaging device, such as X-ray imaging, may be used so as to ensure appropriate positioning and fixing of the pin, e.g., along the frontal or sagital plane. As illustrated in FIG. 13, once the pin 202 has been appropriately positioned, an awl, such as a square awl 204, may be positioned and slid over the pin 202 in a manner sufficient to puncture the cortical part of the pedicle so as to facilitate the insertion of a drill. A protection sleeve may then be positioned, if desired, so as to facilitate delivery of a tube guide.

Figure 14:
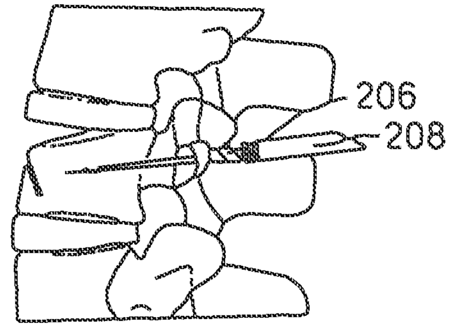
Figure 15:
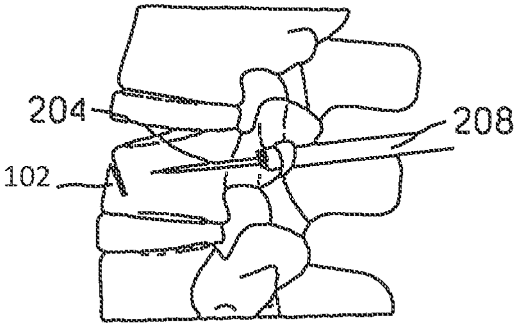
Figure 16:
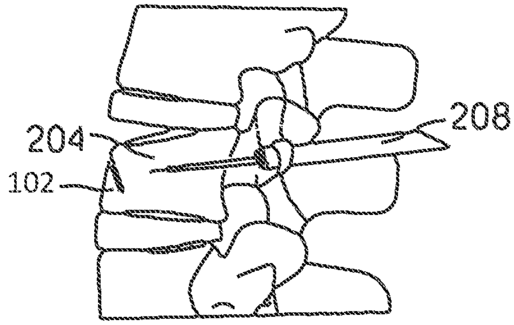
FIG. 16 illustrates a side view of a vertebra with a tube guide inserted there through and associated with the vertebra.

As can be seen with respect to FIG. 14, a drill 206 may be assembled and positioned at the delivery site. For instance, the drill 206 may be assembled in part applying a brake washer and tube guide 208 thereto and the entire assembly may be positioned over the pin. For example, the positioning of the drill 206 may be such that it allows the tube guide 208 intermediate guidance compared to the pin. The use of an imaging device, such as X-ray imaging, may be used so as to ensure appropriate positioning of the drill and/or tube guide, e.g., along the frontal or sagital plane. Such imaging may be important so as to prevent rupture of the pedicle. As illustrated in FIG. 15, the tube guide 208 may be positioned so as to be inserted into the pedicle proximal cortical and affixed thereto, for instance, by screwing. For example, the tube guide may include 1, 2, 3, or more threads, such as at 120°, which allow the tube guide 208 to be stabilized within the pedicle. Specifically, the tube guide may be inserted through the soft tissue by applying a counter clockwise force thereto, however, the fixing thereof to the bone may be via clockwise motion (e.g., clockwise screwing). Once the tube guide 208 has been fixed into the pedicle proximal cortical, the pin may be removed, e.g., before drilling, as illustrated in FIG. 16.

Figure 17:
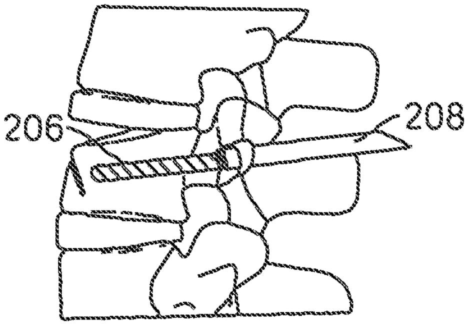
Figure 18:
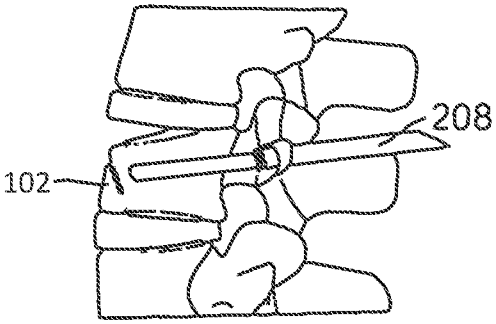
FIG. 18 depicts the vertebra of FIG. 17 with the drill removed.

Once the drill 206 has been appropriately positioned, as illustrated in FIG. 17, both the pedicle and the vertebra body 100 may be drilled in such a manner so as to produce an intra-osseous cavity with selected dimensions for delivery, positioning, and/or expansion of the device. Once the vertebra body 100 has been drilled, the drill may be removed, as illustrated in FIG. 18. If desired, a probe can be used to check the access and/or delivery site.

Figure 19:
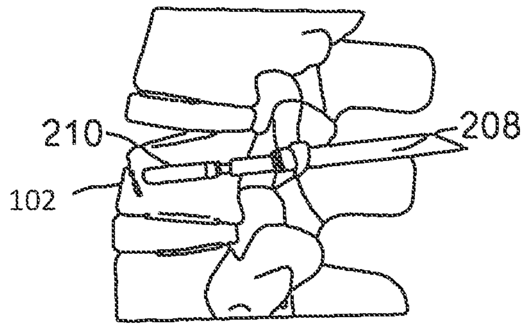
Figure 20:
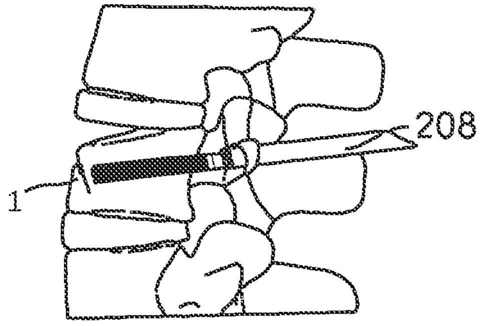
FIG. 20 depicts the vertebra of FIG. 19 with the device gauge removed.

A gauge 210 may be inserted into the prepared access as illustrated in FIG. 19. The device gauge 210 may be inserted into the access so as to prepare the device site. For instance, adjustment of the depth can be effectuated so as to ensure optimal positioning of the device. The device gauge 210 may then be removed as illustrated in FIG. 20. A probe may be used to assess the configuration of the access and/or implant bed, e.g., cavity, prior to insertion of the device.

Figure 21:
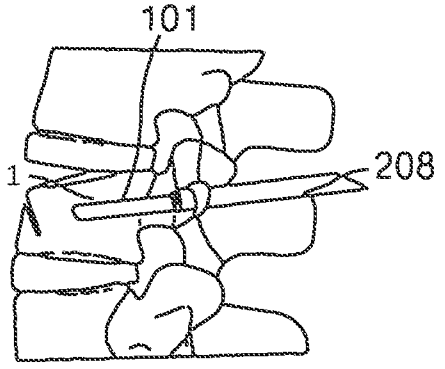
Figure 22:
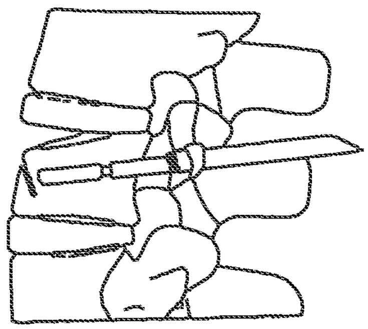
FIG. 22 illustrates a vertebra with an implanted device inserted therein.

FIG. 21 illustrates the insertion of the device 1. The device 1 is affixed to a holder 101 and the affixed assembly is inserted into and through the access hole prepared by the drill, for instance, until the brake washer is stopped by the tube guide. As illustrated in FIG. 22, the device 1 may then be adjusted, for example, in a manner so that its plane of expansion is parallel to the vertebra mechanical axis, e.g., the device expansion may be parallel to the device holder handle.

Once appropriately positioned, the device 1 may be brought from the non-expanded state into the expanded state to restore the vertebral height, as has been illustrated with reference to FIG. 1.

Figure 23A:
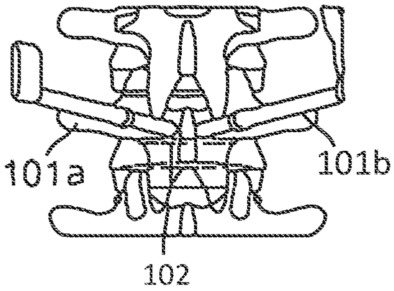
FIG. 23 depicts the vertebra of FIG. 10 with an additional access there through, which additional access includes a trocar there through and the original access includes a cannula plug.
Figure 23B:
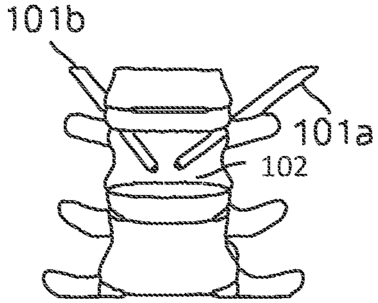

As illustrated in FIGS. 23A and B, the method of surgery described with respect to FIGS. 10-22 may be repeated for the implantation of one or more additional expandable implantable device at a second location in the bone. For instance, through a second pedicle a second implantable device may be inserted into the vertebra 102. As illustrated in FIGS. 23A and B, a second pedicle in vertebra 100 may be accessed for delivery and implantation of a second expandable device. A forward view of the vertebra 100 with one holders 101*a* and a cannula plug inserted into vertebra 100 through two different pedicle access points is shown in FIG. 23 A. FIG. 23B shows a rearward view of the vertebra 100 of FIG. 23B, with two holders 101*a* and 101*b* inserted into the vertebra 100. As shown, holders 101*a* and *b* include respective expandable implantable device 1. Once inserted and appropriately positioned within the vertebra 102, the device may be expanded, e.g., progressively, in order to reduce the fracture and/or re-establish at least partially or completely the original height of the vertebra. It is noted that the device may also be expanded at the same time, if desired. The reduction of the fracture may be imaged, by methods well known in the art, such as by X-ray imaging or fluoroscopic monitoring. After the desired expansion has been achieved, the device holder(s) may release the device(s), e.g., by unscrewing the expansion handle, from the device and the device holder(s) may be.

FIG. 24 shows a set of cores 7', 7", 7"" for fixating blocks for the device with different sizes. These may be provided in a kit of parts which also contains an expandable implantable device, such as in the examples. During surgery, the operating medical practitioner can select a suitable block of the set, which fits into the intra-block space 12 created during the surgery. The medical practitioner can then place the selected block in that space 12. Alternatively or additionally, the set may comprise complete fixating blocks 5 of different size, and as explained an appropriate one be selected to fit into the inter-block space 11 created during surgery.

Such a set or kit, or just the device may be provided in a single package. The package may further comprise an enclosure and instructions for using or an indication of usability of the member in a method of bone surgery on a mammal. For example the instructions or indication may be for repairing fracture, or treating osteoporosis. The package may e.g. be a sterile package in which the mentioned objects are sealed to remain sterile.

The example illustrated in FIGS. 25-30 may equally be provided in such a package. This example is the same as the examples of FIGS. 2-4; 5-8 and 9 except for the following.

Figure 25:
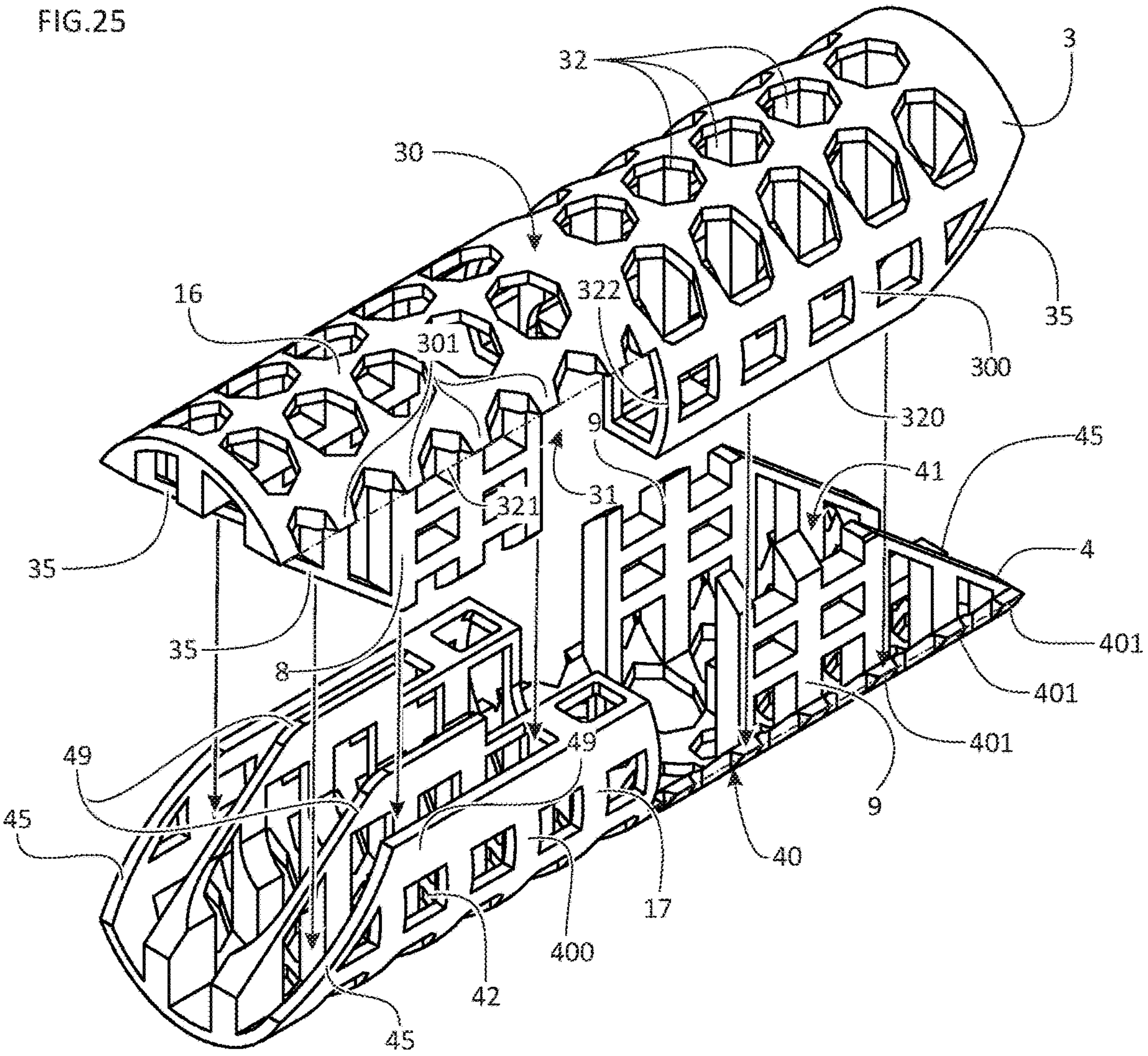
FIG. 25 shows a perspective, exploded view of examples of bulk blocks suitable for an expandable implantable device.
Figure 26:
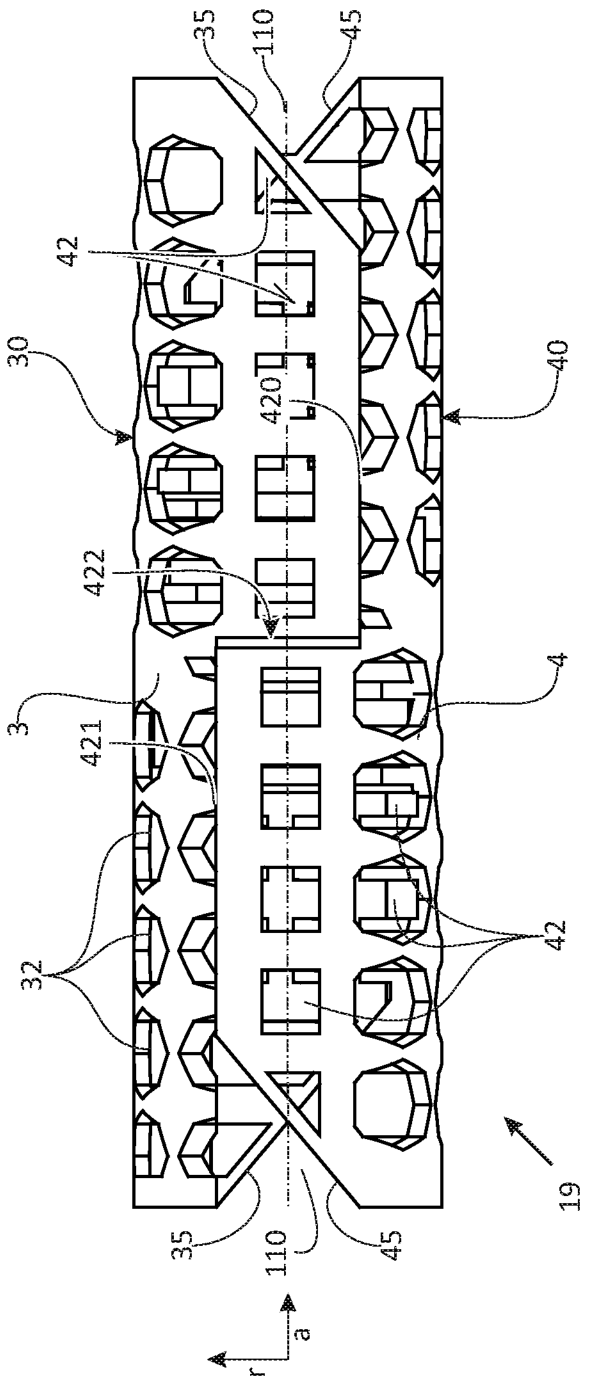
FIG. 26 shows a side view of a device body in the non-expanded state formed from the blocks of the example of FIG. 25.

In the example of FIGS. 25 and 26, a load bearing block 3 and shielded block 4 are shown, which have complementary bone side surfaces 30, 40, which in the non-expanded state, when the inter-block space sides 31, 41 touch each other, form the outer surface of a device body 19. More specific, each of the bone side surfaces 30, 40 have an elongated shape which extends from a first transversal end to a second, opposite transversal end, with lateral edges 320-322 resp. 420-422 between the transversal ends defining the lateral sides of the bone side surfaces. The bone side surfaces 30, 40 are curved in the transversal direction, around their longitudinal axis and thus each defines a cavity with the open side facing towards the other block. Said differently, each block 3, 4 forms a partial device body of which an inside interfaces with the other block, and of which the bone side surface 30, 40 defines the other, outwards facing side. When the blocks 3, 4, are placed with the bone-side surfaces 30, 40 contacting each other over the lateral sides, i.e. the edges 320-322, 420-422 abutting, as illustrated in FIG. 26, the blocks 3, 4 together form a device body 19, which in the circumferential direction is continuous and the bone-side surfaces 30, 40 together enclose, the inside of the device body 19 in a sleeve-like manner. More specific, in this example the contact over the lateral edges results in a flush overall surface, where the bone-side surfaces 30, 40 are level with each other at the lateral edges. Thus, the device body 19 has a smooth shape. Moreover, in this example, the casing is in the axial direction, indicated with arrow a in FIG. 26, of the unexpanded implant, free of discontinuous steps or projections. This allows to insert the expandable implantable device in the unexpanded state smoothly through an access into the vertebra or other bone. Although other shapes may be used, in the present example, the body 19 has a circle cylindrical shape, but alternatively this may be e.g. a non-circular elliptical cylindrical or other suitable cylinder, such as a hexagonal or other polygonal cylinder, and generally another elongated shape, such as a fusiform, cigar-shape or lemon-shape or a rectangular cuboid. Preferably the shape has rounded edges.

As shown, the bone side surface 30, 40 of each of the blocks is a section of the outer surface of the device body 19, defined by a sectional plane non-parallel to the radial direction and in this example extending through the axial ends of the device body 19. More specifically, the section plane which separates the two bone side surfaces is parallel to the longitudinal axis of the device body 19, and in this example perpendicular to the direction of movement of the blocks 3, 4 (indicated with arrow r in FIG. 26). The combined blocks have complementary shapes which together, when the edges 320-322|420-422 are correctly placed onto each other and the insides of the blocks 3, 4 are positioned interdigitated into each other, form the complete device body 19, e.g. the cylindrical or other elongated shape. In this example, the section is, in the longitudinal direction discontinuous, that is the sectional plane has a step. Thus, the lateral edge of each of the bone side surfaces 30, 40 exhibits in the longitudinal direction a step 322, 422 which separates a first part 420 from a second part 421 of the edge. In the first part 320, 420, the edge is located, seen in the transversal direction, further from the longitudinal axis of the surface 30, 40 than in the second part 421, where the edge lies closer to the longitudinal axis of the bone side surface 30, 40. Said differently, the step 322, 422 separates a first side of the bulk block 3, 4 where the bone side surface 30, 40 has side lobes 300, 400 and encloses a larger section of the inside, from a second side where the bone side surface 30, 40 encloses a smaller segment. It will be apparent that this transition may likewise be gradual, and that the side lobes 300, 400 may e.g. have a curved edge.

Each bulk block 3, 4, has at the inter block side surface 31, 41 a matrix or matrices 8, 9 of unit cells which can be admitted in the inside of the other bulk block. Like the example of FIG. 9, in this example the blocks 3, 4 are interdigitated in the non-expanded state, and are movable relative to each other in the radial direction indicated in FIG. 26 with the arrow r, to take the mutually interdigitated parts out of each other. However, instead of the fingers, i.e. the ribs, extending transversely as in the example of FIG. 9, in the example of FIGS. 25 and 26, the ribs extend in the longitudinal direction.

In FIGS. 25,26 each block 3, 4, has its inside divided in parts 16, 17. In a first part 16 one or more porous elements, in this example panel shaped submatrices of the matrices 8, 9, are located. A second part 17 of the inner space is partitioned in slots in which the porous elements of the other block can be admitted. In FIG. 25, the part 16 with the porous elements is at a distance from side lobes 300, 400 of the surfaces 30, 40, and, seen in the lateral, also referred to as longitudinal, direction of the bulk blocks 3, 4, a gap is present between the lobes 300, 400 and the porous elements. The in slots divided part 17 of the inner space is divided in slots by ribs, of which only the ribs 49 of the shielded block 4 are visible in FIG. 25. In a slot, a porous element can be admitted. The ribs 49 project from the inside of the bone side surface 30, 40 inwards, parallel to each other and the direction of expansion. Thus, the ribs 49 guide during the expansion the movement of the porous element and hence of the other block 3, 4 until the porous elements are out of the slots.

In this example of FIGS. 25 and 26, the ribs 49 extend parallel to the axial direction of the implantable device 1, from a respective axial end of the bulk block 3, 4 inwards towards the other axial end, and the blocks are open at the axial ends. Thus, the ribs 49 provide an open structure which in the expanded state facilitate bone-in growth and on-growth, and in the non-expanded state firmly holds the matrixes in the slots. The ribs 49 are further provided with passages through which the slots are communication. This allows the ingrowing bone to propagate between slots, and hence enhances the osseointegration after implantation. However, the overall structure is still very strong despite its openness and can withstand the compressive, external loads exerted during implantation and afterwards. Although the ribs 49 can be implemented differently, in the shown examples the passages in the ribs are implemented as sides of unit cells, and accordingly the ribs 49 together form a respective matrix of unit cells, and thus a submatrix of the matrix 8, 9 of the bulk block 3, 4.

The porous panels in the shown examples are shaped as panels with a submatrix of the matrix 8, 9, and each panel has a shape which fits into the slot of the other block 3, 4. The overall matrix 8, 9 in this example is thus formed by an arrangement of the submatrices, the panels, present at one side of the gap and the submatrices, the ribs, at the other side of the gap. In this example, the matrix further includes the side-lobes which are equally provided with open sides of unit cells. Accordingly, in this example, when the panels are in the slots, the matrix of each bulk block 3, 4 extends through a matrix of unit cells of the other bulk block 3, 4. The overlapping parts of the matrixes 8, 9 then comprise the porous elements, the ribs and, if present the side lobes.

As further shown, the panels are shaped as elongated matrix blocks and located at the other end of the bulk block 3, 4, other than that the end where the ribs 49 of that bulk block are located. These matrix blocks extend from the axial end opposite to the axial end where the ribs 49 are located towards the ribs 49 and are in the transverse direction located at the same position as the slots, thus allowing the matrixes to be placed in the slots of the other block without off-setting of the sections, and hence without deformation of the complete shape of the combined pre-shaped blocks 3, 4.

As shown in FIG. 25, in the transverse direction, the matrix blocks 8, 9 are spaced apart, as are the ribs 49, and in each block a central slot is present in the non-expanded state which extends from one of the axial ends up to the other axial end. Through the central slot an actuator 18 or other object can be inserted to project at both axial ends out of the implantable device 1, as illustrated e.g. in FIGS. 29 and 30 with the threaded rod. In the transverse direction, the matrices 8, 9 are slightly recessed relative to the lateral edge of the bone side surface 30, 40. In this example, as indicated with reference numbers 401 in FIG. 25, the surface 30, 40 has at the lateral edge, in the area of the matrices 8, 9, nobs 301, 401 projecting in the transverse direction beyond the matrix block. In the non-expanded state, the side-lobe 300, 400 of the other block covers the matrices, and abuts to the projecting nobs 401 of the edge. Thereby, in the non-expanded state a relatively high rigidity is obtained without requiring voluminous structures.

In FIG. 25, the bone side surfaces 30, 40 are porous and provided with respective open cells 32, 42. As shown, each of the surfaces 30, 40 is provided with multiple types pores. In this example the pores at the side lobes 300, 400 differ from the pores more towards the centre of the surfaces 30, 40. The side lobes 300, 400 have rectangular unit cells whereas the pores on the other parts of the surfaces 30, 40 are heptagonal. Furthermore, the pores at the side lobes 300, 400 are smaller than in the centre of the surfaces 30, 40. Thereby, an open structure obtained is obtained which is still very strong and capable of resisting the loads acting thereon during implantation and expansion.

As best seen in FIG. 26, the axial ends of each of the two blocks 3, 4 are chamfered such that when the two blocks 3, 4 are slid on to each other, e.g. in the non-expanded state of the device 1, the chamfered ends of the blocks project and between the projecting ends 35, 45 a notch 110 is formed on which an actuator 18 can engage, as explained below in more detail. In these examples, the chamfered ends 35, 45 are formed by inclined axial sides of respectively the ribs 49 and side lobes 300, 400 at one of the axial ends and by inclined axial sides of the matrices 8, 9 at the other axial end.

Figure 27:
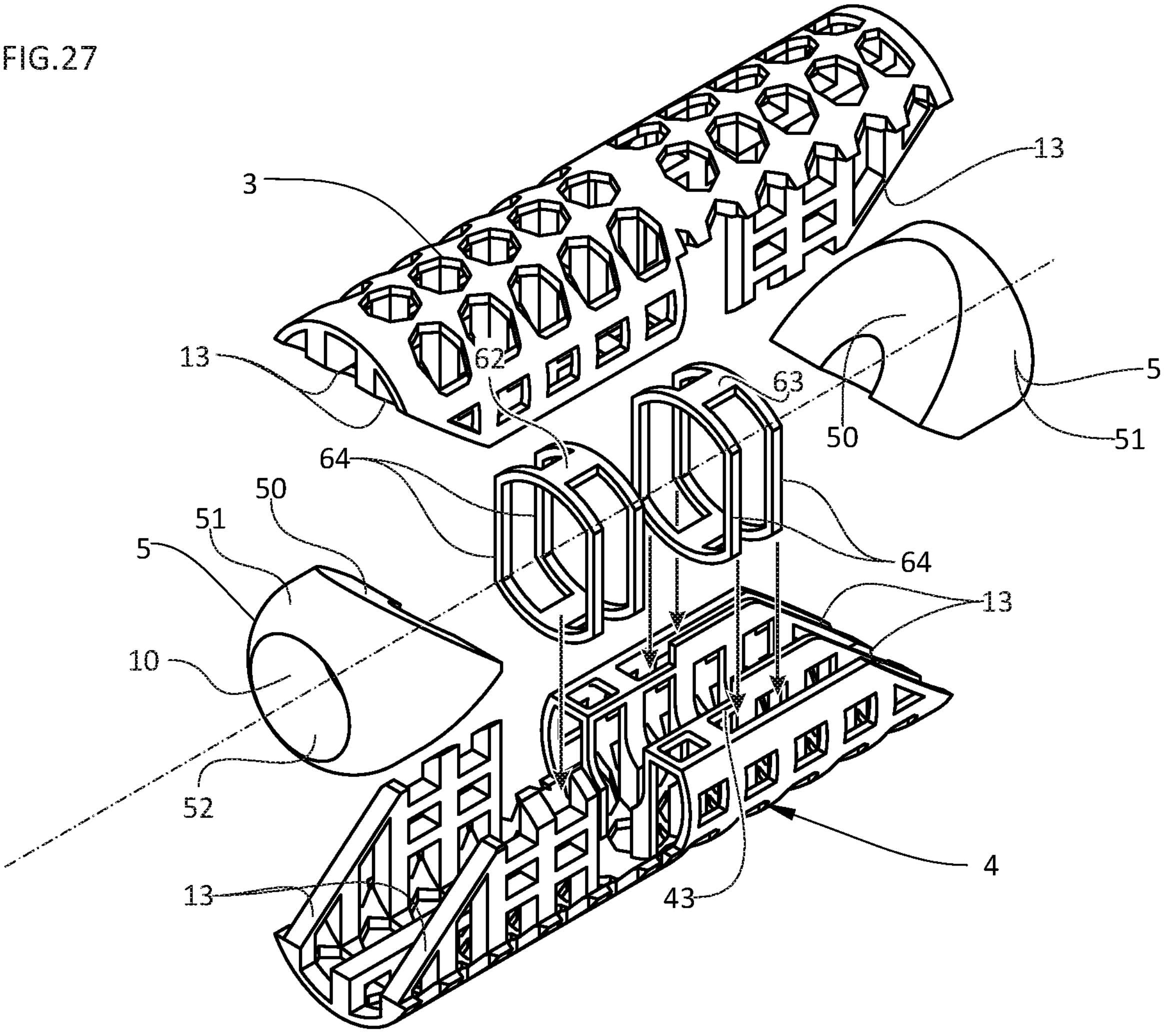
FIG. 27 shows an exploded view of an assembly of frame and pre-shaped fixation blocks and the examples of FIG. 25

Referring to FIG. 27, the blocks 3, 4 of the example of FIGS. 25 and 26 may be form-closedly connected to each other by means of respective ring-shaped members 62, 63. In this example, each member 62, 63 comprises two parallel closed loops 64 which are fixated to and spaced apart from each other by a bridge. The loops 64 are in this example shape-retaining, and fixated relative to each other in position and orientation, in this example by the bridge. The loops 64 can e.g. be made from a metal or a hard plastic. Although not shown in this exploded view but as illustrated with the arrows in FIG. 27, each of the ring-shaped member om 63 extends through the pores of the matrix 8, 9 of a respective block, each member forming a closed loop around a respective strud 43, and passing through the matrices. Thus, the rotational movement of the bulk block 3, 4 relative to the respective member 62, 63 is restricted, and preferably blocked. In this example, the loops 64 also pass through the central slot, and through the matrix block at both sides of the slot, but it will be apparent that e.g. each matrix block may be provided with a separate loop, for example.

Figure 29:
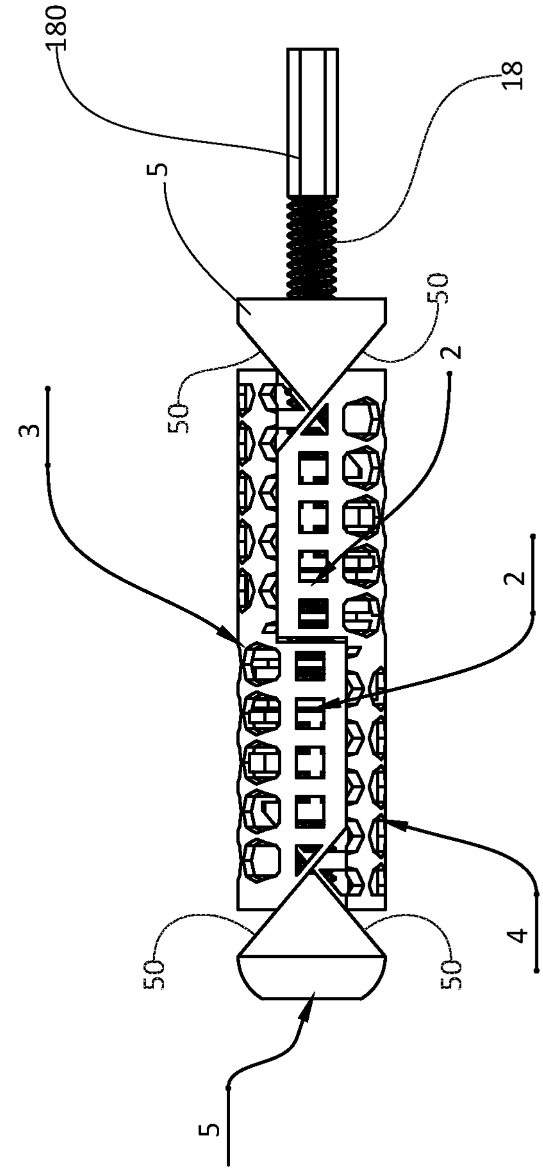
FIG. 29 shows an example of an expandable implantable device assembled with the parts of FIG. 27, in a non-expanded state.
Figure 30:
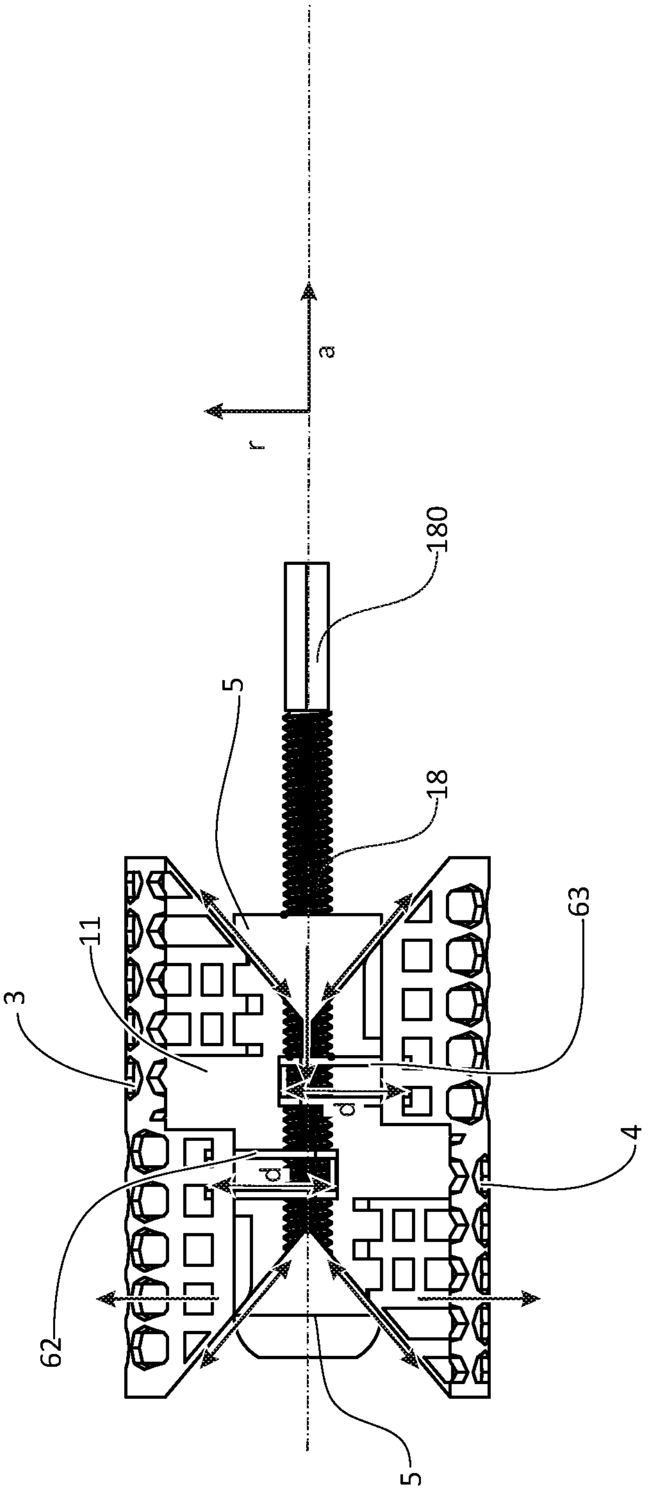
FIG. 30 shows the example of FIG. 29 in an expanded state.

As shown each block 3, 4 further has a gap in which the member 62, 63 of the other block can be admitted. In the example of FIG. 27, the gap is located, seen in the axial direction a, in between the matrices 8, 9 and the ribs 49, and separates the ribs 49 from the matrix blocks of the respective block 3, 4. In this example, the member 62, 63 is admitted in the gap without being attached to the block. Accordingly, the freedom of movement of the bulk block 3, 4 is not restricted by the member 62, 63 (attached to the other bulk block), admitted in the gap. The total range of expansion can thereby be increased. As illustrated in FIGS. 29 and 30, an elongated object can extend in the axial direction through the loops 64 of both members 62, 63. Such an object is form-closedly connected to each of the blocks and thereby a form-closed but movable connection between the bulk block 3, 4 can be obtained with a large freedom of movement. In such a connection, the loops 64 guide the movement of the blocks 3, 4 and define the path along which the blocks can move relative to the elongated object. Preferably, as in the example the connection provide a single degree of freedom, in the radial direction r from the un-expanded state up to the maximum expansion, with other degrees of freedom being limited, e.g. which allows the block 3, 4, to rotate around an axis extending in the radial direction of the body 19 relative to each other over a very limited range of e.g. less than 10 degrees, such as 5 degrees or less, e.g. to some, intentional or unintentional, clearance of less than 2 degrees, for example which in practice is not noticeable.

FIG. 27 further shows fixation blocks 5 which in the axial direction are spaced apart. In this example, at each axial end a fixation blocks 5 is present, and the fixation blocks 5 are translationally movable in the axial direction a. In this example, the fixation blocks 5 have an implant facing side 50 which is shaped to engage in the spacing between the projecting ends 35, 45 at the axial end of the blocks 3, 5. In the expanded state, the fixation blocks are positioned between the bulk blocks 3, 4 and maintain a separation between them and inhibit the bulk blocks 3, 4 from moving towards each other. The fixation blocks 5 thus prevent the implantable device 1 from collapsing back into the non-expanded state, and secure the expanded state. In addition to securing the expanded state when in position, the fixation block 5 further actuate the expansion when the fixation blocks 5 are moved. More specific, the fixation blocks 5 are movable towards each other and the implant facing sides 50 exert, upon contact with the projecting ends 35, 45 and when moving towards each other in the axial direction of the bulk blocks 3, 4, a force on the axial ends of the bulk blocks 3, 4 which pushes the bulk blocks radially outwards. In this example, the projecting ends 35, 45 form an inclined contact surface with the implant facing side 50 and due to the moving force, a pressure is exerted on the contact surface which has a component in the radial direction which causes the bulk blocks 3, 4 to move radially outwards.

As shown e.g. in FIG. 29, the implant facing sides 50 may have a height equal or less than the radial dimension of the device body 19 in the non-expanded state, and preferably the entire fixation block 5 does not project beyond the device body 19 in the radial direction. Accordingly the device 1 has in the non-expanded state a closed shape which can be smoothly inserted in the bone. In this example, in the non-expanded state the implant facing sides contact the inclined surface of projecting ends 35, 45, and close-off the axial ends of the device 1 in the contacting areas. Thus, seen in the axial direction a, the fixation blocks 5 and the device body 19 form a continuous body in the non-expanded state which further facilitates inserting the device 1 into the cavity 116 through the bone.

Although other shapes are likewise possible, in this example the fixation blocks 5 have a wedge-like shape, which tapers from a base towards the other fixation and of which the two surfaces contact each other at a ridge at the implant facing side 50. This shape allows a precise control over the expansion of the device 1. The widest part of the wedge determines the maximum distance over which the bulk block 3, 4, can be pushed outwards. As shown, in this example the wedge-shaped fixation blocks face each other with their sharp sides. When moving the fixation blocks 5 towards each other, the wedge slides over the chamfered projecting edges 35, 45 and pushes the bulk block 3, 4 outwards, in the radial direction r indicated, as illustrated in FIG. 30 with the arrows. Alternatively, the fixation blocks 5 may be oriented with their inclined surfaces turned away from the other fixation block, and the inclined surfaces of the bulk blocks 3, 4 be oriented corresponding, in which case the bulk blocks 3, 4 can be pushed radially outwards by moving the fixation blocks 5 away from each other.

In this example, the base 51 has a shape similar to that of the case, e.g. cylindrical. Through the base a passage 52 extends which, when the device 1 is assembled lies in the prolongation of the central slot and through which e.g. a threaded rod or other actuator 18 (or other object) can extend, and by means of which the actuator can engage on the fixation block 5, although other types of engagement are likewise possible. The actuator 18 engages on the fixation blocks 5 to move then relative to each other, and thereby actuate the movement of the bulk blocks 3, 4 and hence the expansion of the device 1. Since the movement can be controlled precisely, this allows a controlled expansion of the device 1. The passage 52 can be threaded to engage with the threaded rod to actuate the movement of the fixation blocks towards each other, and hence actuate the movement of bulk blocks 3, 4.

Figure 28:
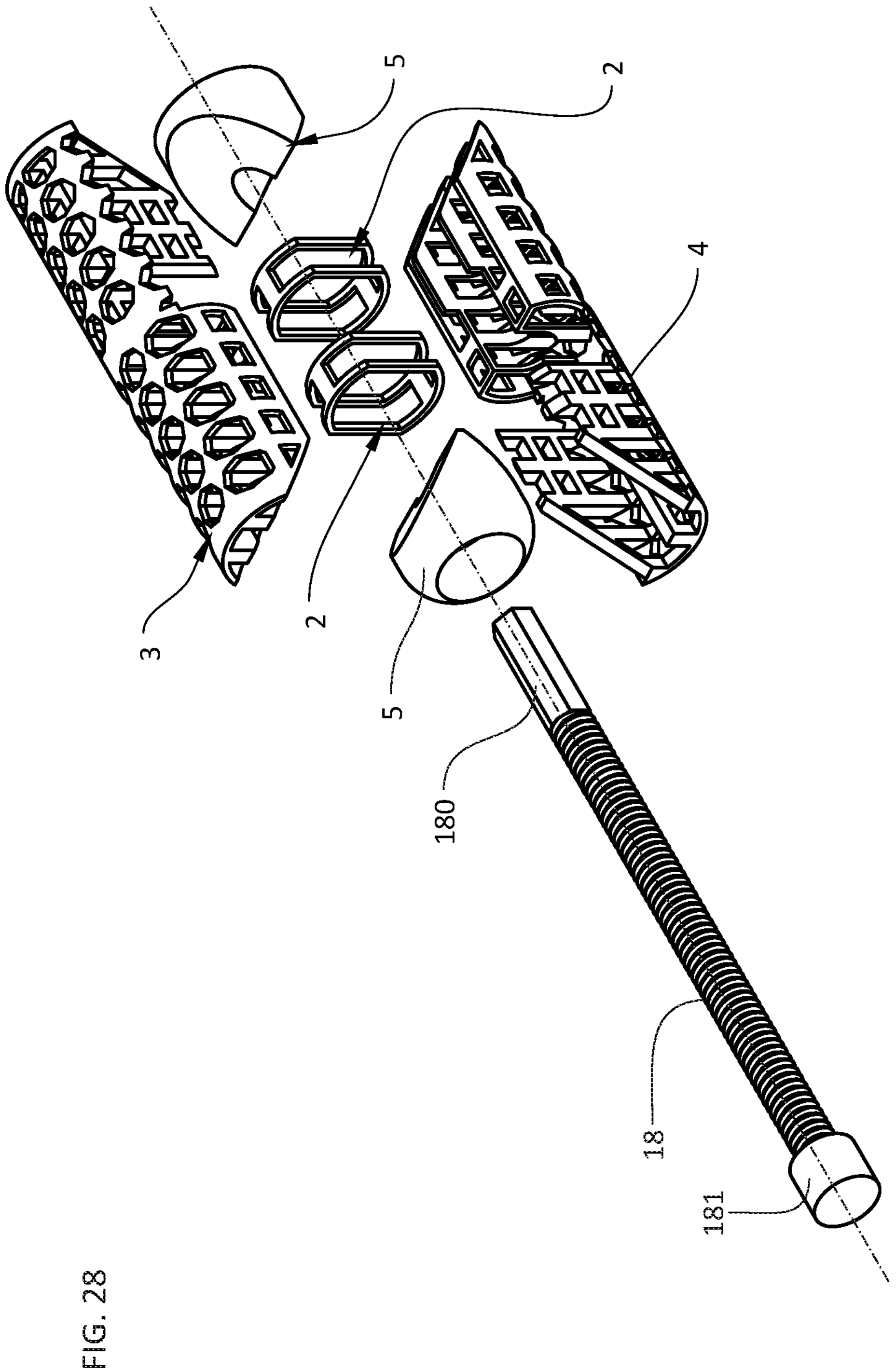
FIG. 28 shows an exploded view of an assembly of the example of FIG. 27 and an actuator.

FIG. 28 shows a threaded rod 18 which can be positioned inserted through the fixation blocks and the closed loops of the ring-shaped members 62, 63. The rod 18 has a hexagonal wrench end 180 on which a compatible socket can be placed to rotate the rod 18 arounds its axis, and it will be apparent that other rotational interfaces are likewise possible, such as a hexagonal socket or a screw-head just to name a view. At the opposite end, the rod has a stop 181 which holds the fixation block 5 at that end in position and prevents the block 5 from moving off the rod 18. As shown more clearly in FIGS. 29 and 30, in the assembled device 1, the rod 18 extends with the end 180 projecting at one of the axial ends, through the central slot, with the stop 181 projecting at the other axial end of the implantable device 1.

As further shown, the rod 18 extends through the loops 64 and thus is form-closedly, but movably, connected to the respective bulk block 3, 4. Since both bulk blocks are form-closedly connected to the rod in this manner, a form-closed connection between the bulk blocks 3, 4 is obtained with a relatively large freedom of movement in the radial direction.

As illustrated in FIG. 29, in the non-expanded state the rod 18 extends through the fixation blocks, and though the loops 64 in the central slot, and retains the fixation blocks in position relative to each other, and form-closedly but movably attaches the bulk blocks 3, 4 to each other. The bulk blocks 3, 4 extend through each other in this state.

By rotating the rod in one direction, the threaded engagement with the fixation blocks 5 actuates a translational movement of the fixation blocks 5 in the axial direction, towards each other. Due to the contact with the inclined surfaces of the bulk blocks 3, 4 the bulk blocks 3, 4 are pushed radially outwards to expand the device 1, out of the non-expanded state. The amount of expansion can be precisely controlled by the rotation of the rod 18. In this respect, it will be apparent that the ratio of rotation of the rod and expansion of the device depends on the angle of inclination of the inclined surfaces as well as the lead of the thread, and that these may be chosen to obtain a desired ratio.

More specific, by rotating the threaded rod, the rod will translationally move relative to the loops 64 which engage with the thread, and hence relative to the bulk blocks 3, 4. The end with the stop is moved inwards into the inter-block space, and hence the fixation block at that location (in FIGS. 29 and 30 at the left-hand side) as well. In this respect, it will be apparent that this fixation block does not engage with the thread and remains in position relative to the rod in this example. At the same time, due to the rotation, the other fixation block, which does engage with the thread, moves over the rod into the inter-block space in the opposite direction, and thus towards the other fixation block, resulting in the expansion of the device 1 as illustrated in FIG. 30. It will be apparent that in this example the loops 64 act as a threaded bore for the threaded rod, and e.g. may be implemented in alternative shapes performing that function, and that another screw-mechanisms causing a linear displacement of the rod relative to the bulk blocks 3, 4 may also be used.

By rotating the rod in the opposite direction, an opposite movement of the fixation blocks 5, away each other, is actuated and accordingly the bulk blocks 3, 4 moved to collapse the device 1 under the exterior load exerted on the bulk blocks. Thus, a precise, and reversable, control of the expansion of the implantable device 1 by a medical practitioner is obtained. The device can thus e.g. be positioned in the cavity, and expanded to a certain extend and then e.g. be slightly retracted to e.g. ensure a sufficiently plastic deformation of the bone by the expansion.

As can be seen in FIG. 30, the loops 64 determine the maximum distance between the blocks 3, 4 in the expanded state. As indicated with the arrows d, the inner diameter of the loops 64 in the direction of expansion, in this example in the radial direction r, determines the maximum displacement of each block relative to the rod in that direction. In this example, the loops 64 are of equal diameter but alternatively, e.g. the side of the wedge facing the shielded block 4 may have a different angle of inclination than the side of the wedge facing the load supporting bulk block 3, such that the ratio of displacement of the load supporting bulk block 3 and the displacement of the shielded block 4 is unequal to 1. In such a case equally the respective loops could differ in diameter.

In FIG. 30, the difference in height of the wedge is larger than the maximum amount of displacement. Accordingly, by displacing the fixation blocks 5 until the maximum displacement of the bulk blocks 3, 4 determined by the inner diameter of the loops is reached, the fixation blocks 5 will exert on the respective block a force in the direction of expansion which is opposed by the force the loops 64 exert on the block and accordingly the bulk block 3, 4 is fixated in position relative to the rod 18.

In the foregoing specification, the invention has been described with reference to specific examples of embodiments of the invention. It will, however, be evident that various modifications and changes may be made therein without departing from the scope of the invention as set forth in the appended claims, and that the examples are not intended to be limiting and that the claims should not be construed to be limited to the specific examples shown. Also, in the examples, any preference indicated is not meant as limiting, but rather as indicating that various alternatives are possible of which the referred one is currently considered to present a more favourable one.

For instance, the matrices of the overlapping parts, and more generally the parts of the device 1 may be made of any suitable biocompatible material. The material may for example contain a material out of the group consisting of: metals, metal compounds, metal alloys, metal composites, polymers, ceramics and combinations of materials of this group. The biocompatible material can contain a metal out of the group consisting of: titanium, tantalum, niobium, stainless steel, cobalt chrome alloys, zirconia, or a compound, alloy or composite thereof. Other suitable biocompatible materials can contain a polymer out of the group consisting of polyaryletherketone, polyether ether ketone, polyetherketoneketone.

Also, in the examples of FIGS. 25-30, the blocks 3, 4 are similar, in this example exactly the same. However, depending on the specific implementation, the load bearing block 3 may differ from the shielded block 4. For instance, the shielded block 4 may comprise ribs 49 and slots at both axial ends and the load bearing block matrix blocks at both axial ends which fit into the slots. Likewise, in these examples the blocks are symmetrical parts out of which the device body 19 is composed, but it will be apparent that e.g. the device body may have a sectional plane without step, parallel but no coinciding with the longitudinal axis which divides the parts, for instance.

Furthermore, although in the examples the porous parts are implemented as regular matrices, alternatively some or all may be irregular matrices. Also, in the examples all cells of the matrices are open, but alternatively some cells may be closed and parts of the matrices may be non-porous.

It should be apparent that by providing and/or moving the bulk blocks and, if present, the fixating element 6 in a suitable manner, the device 1 can have in the expanded state (in a cross-sectional view perpendicular to a longitudinal direction of the device along which the device is to be inserted) two, or more than two, legs projecting from an axial centre of the device in the non-expanded state. These legs may for example comprise two, or more than two, extending transverse to each other and/or two, or more than two, extending parallel to each other. The device can thus for example have in the expanded state a cross-sectional shape which is for example +-shaped (after insertion of the core 7 in FIG. 7D), T-shaped, I-shaped (as in FIG. 7B), O-shaped (as in FIG. 7D), U-shaped.

Likewise, where a movement of an object is described (e.g. relative to another object) it will be apparent that, unless explicitly specified otherwise, this is a relative movement, and accordingly depending on the chosen reference frame, the object may be moving relative to an observer while the other object is static, the other object may be moving while the object is static relative to the observer or both objects may be moving, but differently, relative to the observer.

Also, the device may be provided as a tangible object. However, alternatively data representing a model of the device may be provided. In such a case the data may be loaded into a data processing device, e.g. an embedded control system or other type computer performing the computer control, and the data processing device operated to control the forming by a manufacturing device to obtain a shape in accordance with the data. The model can be obtained in any manner suitable for the specific implementation. The design may be stored on an, e.g. tangible, data carrier as data loadable in a computer representing a model of the device or assembly is stored. In this respect, the data carrier can for example be a tangible, non-transitory computer readable storage medium or be a computer readable transmission medium. These computer readable media can be permanently, removably or remotely coupled to the computer. The computer readable transmission medium may be a data transmission media such as wired or wireless transmission media, just to name a few. The computer readable storage medium may comprise for example and without limitation, any number of the following: magnetic storage media including disk and tape storage media; optical storage media such as compact disk media (e.g., CD ROM, CD R, etc.) and digital video disk storage media; nonvolatile memory storage media including semiconductor-based memory units such as FLASH memory, EEPROM, EPROM, ROM; ferromagnetic digital memories; MRAM; volatile storage media including registers, buffers or caches, main memory, RAM, etc.

Also, the fixating block 5 of the second example of FIGS. 5-8 contains a core. This may be a non-expandable core but alternatively, the core itself be implemented as a further fixating block which can expand beyond the intra-block space 12, and the further fixating block have as core yet another expandable fixating block, and so on and so on. This allows a gradual expansion and a flexible shape of the expanded device and accordingly allows an improved filling of an intra-osseous cavity.

Furthermore, in the examples the matrices are open at all sides. However, it will be apparent that in some applications, one, or more than one or all of the matrices may have one, or more than one closed outer surfaces and that e.g. some sides may be closed without any pores.

Also, the fixation block and the bulk blocks may be implemented in any manner suitable for the specific implementation. One, or more than one, and preferably each of the blocks can for example be a monolithic element, and may be made of a single piece of material. This provides a strong block capable of withstanding the forces occurring during implantation and post-implantation. Alternatively, one, or more than one of the blocks may be made of multiple pieces attached to each other, e.g. in case the respect block is allowed to disintegrate during use.

The upper or load supporting bulk block 3 may, for example be made of the same material(s) as the bottom or shielded bulk block 4. This allows manufacturing of both blocks at the same time, e.g. using an additive manufacturing. Alternatively, the blocks may differ in materials from which they are made. This allows, e.g. a rigid first block and a flexible second block. One, or more than one, or all of the blocks may be non-degradable in-vivo or in-situ. This allows a permanent structure, for example in case it is estimated that permanent support to the bone is required and that bone regeneration post-implantation will not be sufficient.

Alternatively or additionally, one, or more than one, or all of the pre-shaped blocks 3-5 may be bio-degradable in-vivo. This allows e.g. to place a temporary device, or a device with temporary parts, without requiring surgery to remove the device. For example, the core 7 or the complete fixation block 5 may be non-degradable, while the bulk blocks 3, 4 are of a degradable material. This allows e.g. a permanent support in case it is estimated that the bone will only partially regenerate at the outer parts of the cavity 106, but not sufficiently in the centre of the cavity 106. The degradable block can then disappear while the cavity space around the non-degradable block fills by bone regrowth.

Moreover, the terms “front,” “back,” “top,” “shielded,” “over,” “under” and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word ‘comprising’ does not exclude the presence of other elements or steps then those listed in a claim. Furthermore, the terms “a” or “an,” as used herein, are used as meaning “one, or more than one”. Also, the use of introductory phrases such as “at least one” and “one, or more than one” in the claims should not be construed to imply that the introduction of another claim element by the indefinite articles “a” or “an” limits any particular claim containing such introduced claim element to inventions containing only one such element, even when the same claim includes the introductory phrases “one, or more than one” or “at least one” and indefinite articles such as “a” or “an.” The same holds true for the use of definite articles. Unless stated otherwise, terms such as “first” and “second” are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

LIST OF REFERENCE NUMBERS

1 device
2 frame
3, 4 bulk block
5 fixation block
6 fixation element
7 core
8 first matrix
9 second matrix
10 actuator interface
11 inter block space
12 intra-block space
13 fixation interface
14, 15 axial end
16, 17 part of bulk block
18 actuator
19 device body
21 guide rod
22 transverse rods
30, 40 bone side surface
31, 41 inter block space side surface
32, 42 open cells
33, 43 cell strut
33' transverse strut
34, 44 open face
35, 45 projecting part
36, 46 fingers
37, 47 passage
38, 48 bar
49 ribs
50 implant facing side
51 base
52 passage
60 fixation element guide
61 ring-shaped member
62, 63 ring-shaped members
64 closed loop
100 pedicle
101 holder
102 vertebra
103 intervertrebral disc
104 vertebra
106 intra-osseos cavity
108 passage
109 endplate
110 notch
111 anterior wall
180 end
181 stop
200 trocar
202 pin
204 awl
206 drill
208 tube guide
210 gauge
300, 400 side lobe
301, 401 nobs
320, 420 part of lateral edge
321, 421 part of lateral edge
322, 422 step

What is claimed is:

1. An implantable expandable intra-vertebral support device for a vertebra of a human or non-human mammal, the device having a non-expanded state in which the device is implantable in an intra-osseous implant cavity of a vertebra of a human or non-human mammal, the device having a non-expanded shape in the non-expanded state, and an expanded state in which the device is configured for supporting, in the intra-osseous implant cavity, the vertebra to resist a spinal load acting on a vertebral end plate of the vertebra and the device is configured for preventing collapse of the vertebra under the spinal load, the intra-vertebral device comprising:

at least two pre-shaped bulk blocks configured for filling up at least a part of the intra-osseous implant cavity when the device is in the intra-osseous implant cavity, and the device is in the expanded state, each of said pre-shaped bulk blocks being movable along a pre-defined path to project outward, relative to the non-expanded shape of the device, when the device is in the expanded state, and each of said pre-shaped bulk blocks comprising a load supporting surface which when the device is provided in the intra-osseous implant cavity with the load supporting surface facing a vertebral endplate and the device is in the expanded state bears a load exerted by the vertebra on the bulk block, caused by an external load acting on the vertebra; and the intra-vertebral device further comprising a pre-shaped fixation configured to be located between the pre-shaped blocks when the device is in the expanded state and is configured to inhibit the pre-shaped blocks from moving towards each other against the load and to further inhibit the device being in the expanded state from collapsing from the expanded state into the non-expanded state;

the intra-vertebral device further comprising a guide which defines the pre-defined path along which the bulk blocks are moveable, the guide comprising at least one loop-shaped frame to which the bulk blocks are movably attached in a form-closed connection, the frame comprising at least a first and a second guide rod along which the bulk blocks are movable, the guide rods extending in the direction of movement of the bulk blocks and each having a first guide rod end and a second guide rod end, said guide rod ends defining a range of motion of the bulk blocks, and the frame further comprising at least a first and a second transverse rod configured to limit the range of motion of the bulk blocks and the first transverse rod connected to the first guide rod ends of the first and second guide rods, and the second transverse rod connected to the second guide rod ends of the first and second guide rods.

2. The device of claim 1, wherein a combined volume of the bulk blocks in the expanded state is larger than the combined volume in the non-expanded state.

3. The device of claim 2, wherein a first of said bulk blocks extends in the non-expanded state through a second of said bulk blocks and moves out of the second bulk block when the device is expanded.

4. The device of claim 3, wherein each of the bulk blocks has a comb-shaped inter-block space side with a plurality of ribs and wherein the ribs of the blocks are interdigitated in the non-expanded state.

5. The device of claim 2, wherein at least one of the blocks has ribs which partition at least a part of the inter-block space side in slots, and at least one other of the blocks has a porous element which in the non-expanded state extends in the slot, the ribs extending in a longitudinal direction of the device.

6. The device of claim 5, wherein the porous elements are panel shaped submatrices of the first and second matrices.

7. The device of claim 2, wherein the ratio of the combined volume in the expanded state and the combined volume in the non-expanded state has a maximum of 2.

8. The device of claim 5, wherein the ribs are provided with passages through which the slots are communication.

9. The device of claim 1, wherein the bulk blocks comprise:

a load facing block with a load facing side on which the load supporting surface is provided, and a shielded block at another side of the load facing block, the shielded block comprising a bone interfacing surface facing away from the load supporting surface; and wherein the bulk blocks are movable in a direction from the load supporting surface to the interfacing surface or from the interfacing surface to the load supporting surface.

10. The device of claim 9, wherein:

the shielded block comprises a first matrix of unit cells;

the load facing block comprises a second matrix of unit cells;

in the non-expanded state the first matrix extends with a first overlapping part of the first matrix of unit cells through at least a second overlapping part of the second matrix of unit cells; and the first and second matrix are movable relative to each other to reduce, when transferring the device from the non-expanded state to the expanded state, the size of the overlapping part and the second overlapping part and to change a combined shape of the shielded block and the load facing block.

11. The device of claim 10, wherein:

in the first overlapping part, each cell comprises struts which form the edges of the faces of the cell, and of the struts all transverse struts extending transversely to a direction of movement of the bulk block are interrupted, to allow passage of the second overlapping part.

12. The device of claim 11, wherein the struts comprise parallel struts extending in the direction of movement, and wherein the parallel struts are uninterrupted.

13. The device of claim 10, wherein:

the second overlapping part comprises a submatrix of the second matrix of unit cells in which each cell is formed by open faces of which the edges are defined by an uninterrupted enclosure of struts, and the second overlapping part extend through the interrupted struts of the shielded block in the non-expanded state.

14. The device of claim 1, further comprising:

an actuator interface for engaging with an actuator for actuating the movement of the bulk blocks along the pre-defined path; and a guide which defines the pre-defined path along which the bulk block is movable.

15. The device of claim 1, wherein the at least two bulk blocks are movable, from an initial position, away from each other to bring the device in the expanded state and form an inter-block space between the bulk blocks; and wherein the pre-shaped fixation comprises a pre-shaped fixating block for sliding into the inter-block space and for inhibiting, when placed in the inter-block space between the bulk blocks, the bulk blocks from moving towards each other.

16. The device of claim 15, wherein:

the fixation block is a wedge shaped fixation block, which is slidable into the inter block space in a direction perpendicular to the direction of the expansion.

17. The device of claim 1, for treating or preventing vertebral bone collapse, such as caused by osteoporosis or cancer, or fracture, such as caused by trauma.

18. The device of claim 1, dimensioned for percutaneous placement in the vertebra.

19. The device of claim 1, wherein at least one of the pre-shaped bulk block and pre-shaped fixation has at least one of a porous outer surface and a porous bulk part.

20. The device of claim 1, wherein:

the at least two pre-shaped bulk blocks comprise a first bulk block and a second bulk block;

the first bulk block extends in the non-expanded state at least partially through the second bulk block; and when the device is transferred from the non-expanded state into the expanded state the first bulk block is moved at least partially out of the second bulk block.

21. A method of bone surgery on a mammal, comprising use of the device of claim 1.

* * * * *